United States Patent [19]

Ohi et al.

[11] Patent Number: 5,354,753
[45] Date of Patent: Oct. 11, 1994

[54] METHOTREXATE DERIVATIVE

[75] Inventors: Nobuhiro Ohi; Hiroharu Matsuoka; Katushito Miyamoto; Hiroshi Suzuki; Nobuaki Kato; Keiichiro Tsuji, all of Shizuoka; Yasuhisa Takeda, Kanagawa; Masahiko Mihara, Shizuoka; Hiromichi Nishina, Shizuoka; Shin Shimaoka, Shizuoka; Kenichi Akamatsu, Shizuoka, all of Japan

[73] Assignee: Chugai Seiyaku Kabushiki Kaisha, Tokyo, Japan

[21] Appl. No.: 971,773

[22] PCT Filed: Aug. 14, 1991

[86] PCT No.: PCT/JP91/01078

§ 371 Date: Feb. 12, 1993

§ 102(e) Date: Feb. 12, 1993

[87] PCT Pub. No.: WO92/03436

PCT Pub. Date: Mar. 5, 1992

[30] Foreign Application Priority Data

| Aug. 14, 1990 | [JP] | Japan | 2-214691 |
| Aug. 15, 1990 | [JP] | Japan | 2-215639 |
| Sep. 21, 1990 | [JP] | Japan | 2-253466 |
| Oct. 30, 1990 | [JP] | Japan | 2-293107 |
| Nov. 29, 1990 | [JP] | Japan | 2-331845 |
| Apr. 19, 1991 | [JP] | Japan | 3-180626 |
| Apr. 23, 1991 | [JP] | Japan | 3-185943 |
| May 30, 1991 | [JP] | Japan | 3-228158 |
| Jun. 12, 1991 | [JP] | Japan | 3-247141 |
| Jul. 3, 1991 | [JP] | Japan | 3-258301 |
| Jul. 30, 1991 | [JP] | Japan | 3-279047 |

[51] Int. Cl.[5] .......... A61K 31/505; C07D 475/08
[52] U.S. Cl. .......... 514/258; 544/57; 544/58.4; 544/58.6; 544/61; 544/105; 544/243; 544/260
[58] Field of Search .......... 544/57, 58.4, 58.6, 544/61, 105, 243, 260; 514/258, 272

[56] References Cited

PUBLICATIONS

J. Het. Chem. 20, 807, 1983.
J. A. Montgomery et al., "Analogues of Methotrexate", Journal of Medicinal Chemistry, 1979, vol. 22, No. 7 pp. 862–868.
J. R. Piper et al., "Synthesis of α and γ substituted amides, peptides, and esters of methotrexate and their evaluation as inhibitors of folate metabolism", Journal of Medicinal Chemistry, 1982, 25, No 2. pp. 182–187.
A. Rosowsky et al., "Methotrexate Analogues. 33. N δ-Acyl-N α-(4-amino-deoxypetroyl)-L-ornithine Derivatives: Synthesis and in Vitro Antitumor Activity", Journal of Medicinal Chemistry, 1988, 31, No. 7, pp. 1332–1337.
R. J. Kempton et al., "Lysine and Ornithine Analogues of Methotrexate as Inhibitors of Dihydrofolate Reduc-
(List continued on next page.)

Primary Examiner—Mukund J. Shah
Assistant Examiner—Y. N. Gupta
Attorney, Agent, or Firm—Browdy and Neimark

[57] ABSTRACT

Disclosed is a compound represented by the formula:

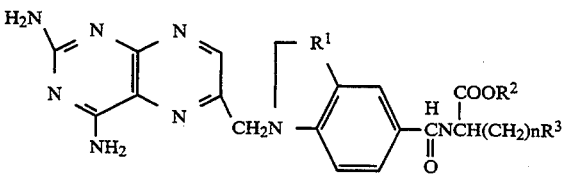

wherein $R^1$: $CH_2$, $CH_2CH_2$, $CH_2O$, $CH_2S$, $CH_2SO$; $R^2$: hydrogen atom, a lower alkyl group having 1 to 4 carbon atoms or a benzyl group; n: an integer of 1 to 4; $R^3$: $COOR^4$, $NHCOR^5$, $CONR^6R^7$, $PO_3H_2$, $SO_3H$.

The compound shows potent antirheumatic function, psoriasis curing function and carcinostatic function and has low toxicity whereby it is available as a medicine.

7 Claims, 12 Drawing Sheets

OTHER PUBLICATIONS tase," Journal of Medicinal Chemistry, 1982, vol. 25, No. 4, pp. 475–477.

J. R. Piper et al., "10-Propargylaminopterin and Alkyl Homologues of Methotrexate as Inhibitors of Folate Metabolism", Journal of Medicinal Chemistry, 1982, vol. 25, No. 7, pp. 877–880.

J. R. Piper et al., "A Synthetic Approach to Poly (-glutamyl) Conjugates of Methotrexate", Journal of Medicinal Chemistry, 1983, vol. 26, No. 2, pp. 291–296.

A. Rosowsky et al., "Methotrexate Analogues. 20. Replacement of Glutamate by Longer Chain Amino Diacids: Effects on Dihydrofolate Reductase Inhibition, Cytotoxicity, and in Vivo Anti Antitumor activity", Journal of Medicinal Chemistry, vol. 26, No. 12, pp. 1719–1725, 1983.

A. Rosowsky et al., "Methotrexate Analogues, 19. Replacement of the Glutamate Side Chain in Classical Antifolates by L-Homocysteic Acid and L-Cysteic Acid: Effect on Enzyme Inhibition and Antitumor Activity." Journal of Medicinal Chemistry, vol.: 27, No. 5 pp. 600–604, 1989.

A. Rosowsky et al. "Methotrexate Analogues. 26. Inhibition of Dihydrofolate Reductase and Folypolyglutamate Synthetase Activity and in Vitro Tumor Cell Growth by Methotrexate and Aminopterin Analogues Containing a Basic Amino Acid Side Chain", Journal of Medicinal Chemistry, 1986, vol. 29, No. 5.

Methotrexate Analogues. 32. Chain Extension, α-Carboxyl Deletion, and -Carboxyl Replacement by Sulfonate and Phosphonate: "Effect on Enzyme Binding and Cell ∝ Growth Inhibition", Journal of Medicinal Chemistry, 1988 vol. 31, No. 7 pp. 1326–1331.

D. F. Worth et al. "Folate Antagonists. 10. Synthesis and Antimalarial Effects of 6-[[(Aryl and aralkyl) amino]methyl]-2,4-pteridinediamines and -pteridinediamine 8-Oxides", Journal of Medicinal Chemistry, 1978, vol. 21, No. 4 pp. 331–337.

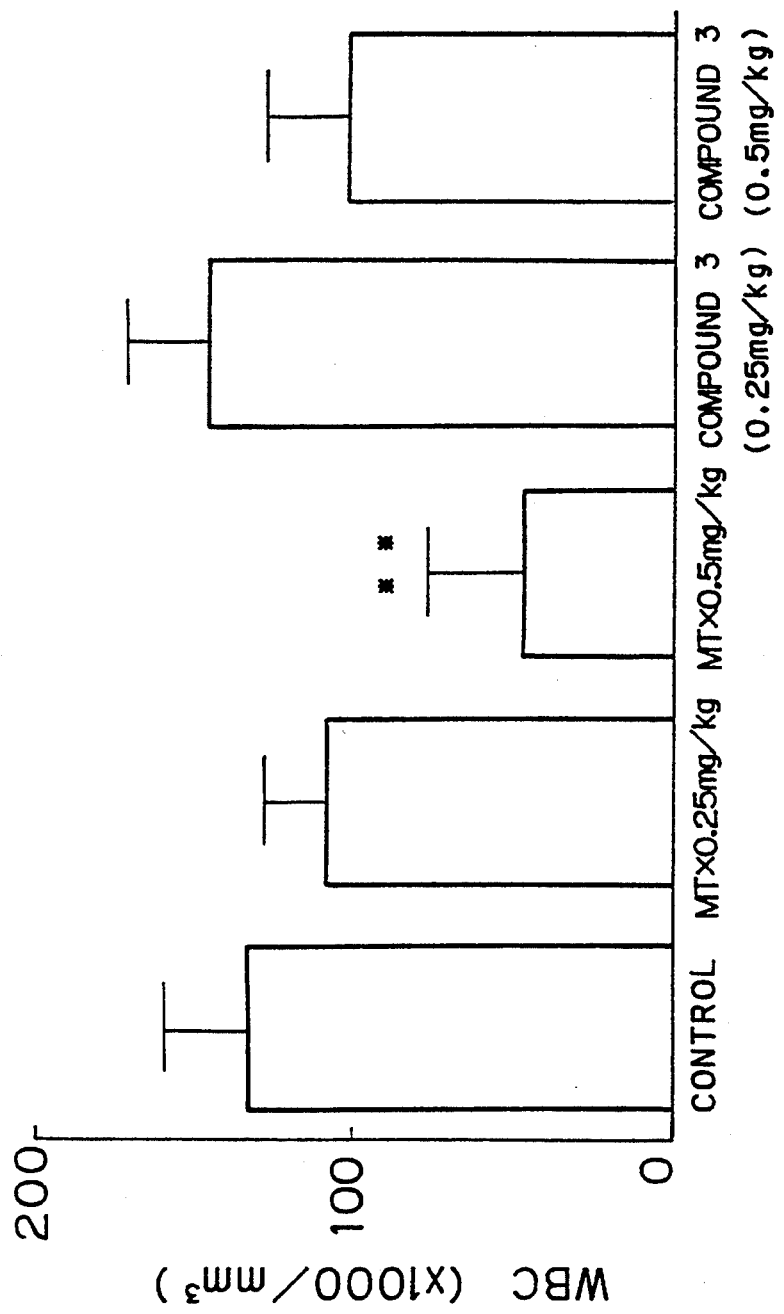

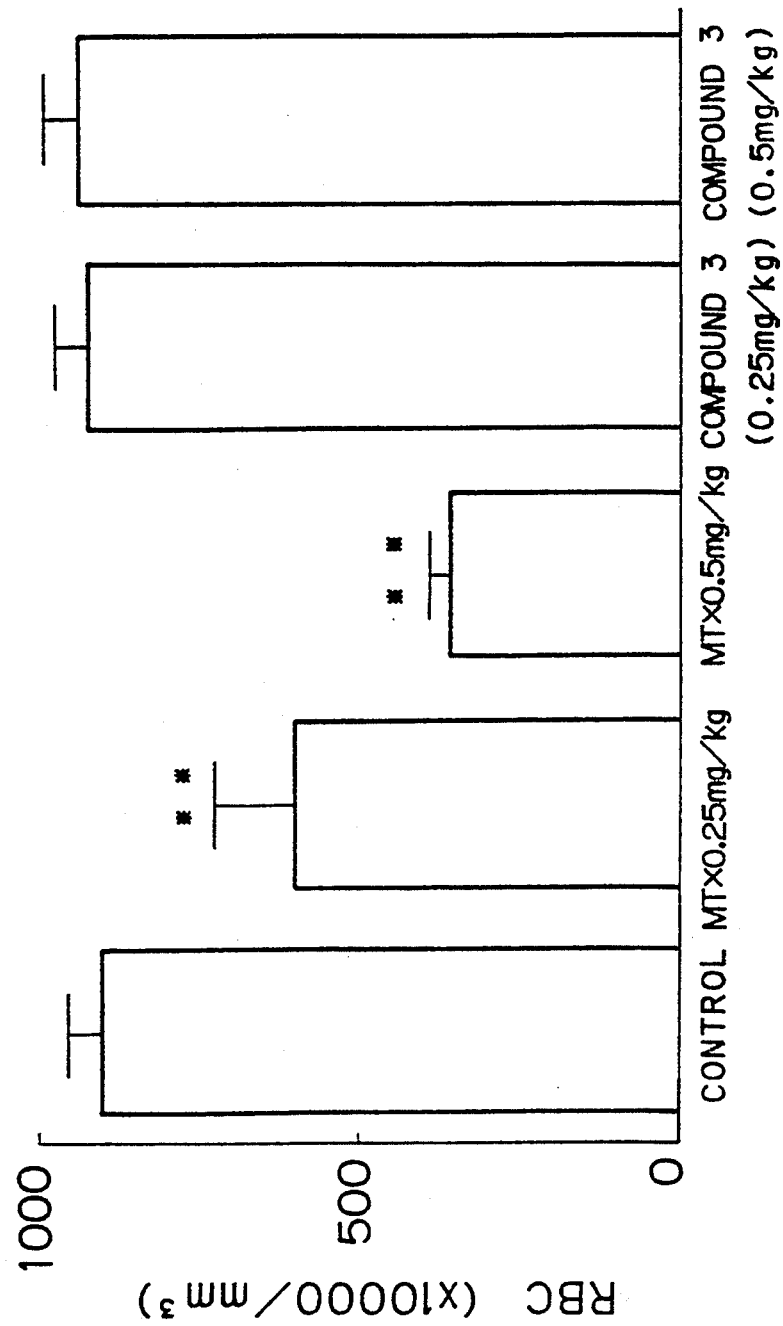

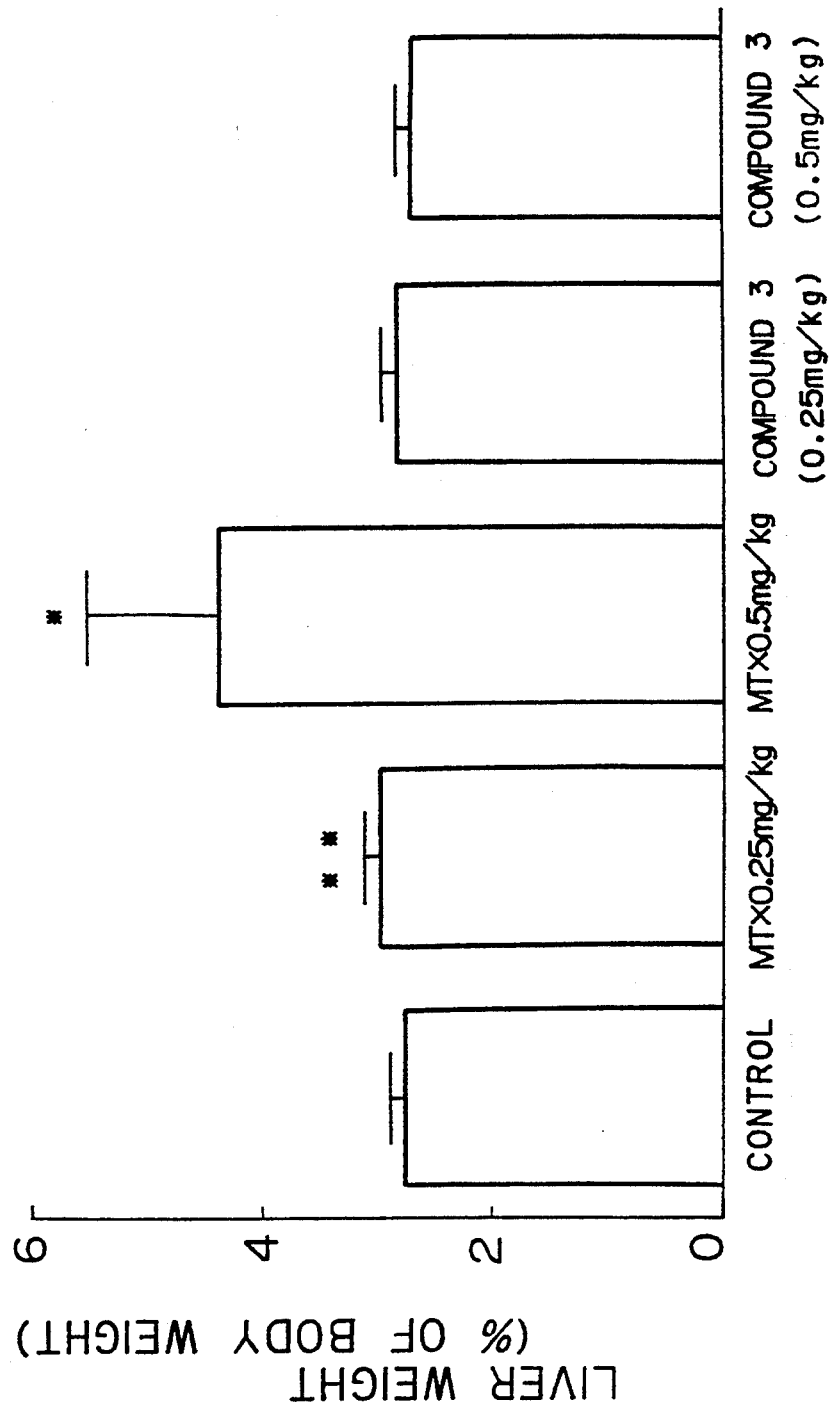

METHOTREXATE DERIVATIVE

BACKGROUND OF THE INVENTION

1. Field of the Invention

This invention relates to a methotrexate derivative, more specifically to a novel methotrexate derivative available as an antirheumatic agent, psoriasis curing agent and carcinostatic agent.

2. Prior art

Methotrexate has been known as a curing agent of leukemia, and Gubner et al. reported its effectiveness for rheumatoid arthritis (RA) or psoriasis in 1951 and it has been used until then as a curing agent of RA in Europe and the United States. Relatively recently, detailed investigations about method of use and dose have been carried out, and it has been clarified that methotrexate therapy in a low dose develops excellent effectivity with a relatively limited side effects. However, side effects such as hepatopathy or fibroid lung caused by the administration of methotrexate cannot be ignored so that a drug having fewer side effects and increased effectiveness has earnestly been desired.

As methotrexate derivatives to which an alkyl group other than methyl group is introduced at $N^{10}$, there have been known for example, the following formula:

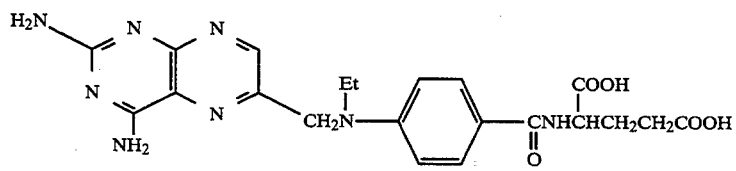

(J. Med. Chem., 22, p. 862 (1979)) or the formula:

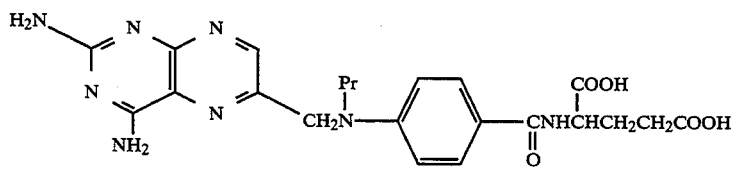

(j. Med. Chem. 25, p. 877 (1982)), and the like, however, they did not necessarily show sufficient activity.

SUMMARY OF THE INVENTION

The present invention is to provide a novel methotrexate derivative represented by the following formula (I):

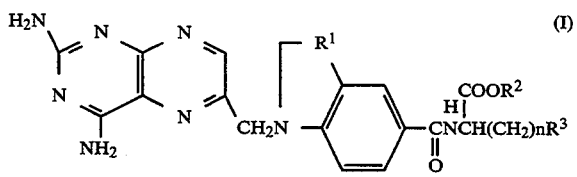

wherein $R^1$ represents one selected from the group consisting of $CH_2$, $CH_2CH_2$, $CH_2O$, $CH_2S$ and $CH_2SO$; $R^2$ represents hydrogen atom, a lower alkyl group having 1 to 4 carbon atoms or a benzyl group; n represents an integer of 1 to 4; $R^3$ represents a group represented by the formula: $COOR^4$ (where $R^4$ represents hydrogen atom or a lower alkyl group having 1 to 4 carbon atoms), $NHCOR^5$ (where $R^5$ represents a phenyl group which may be substituted), $CONR^6R^7$ (where $R^6$ represents hydrogen atom or a lower alkyl group having 1 to 4 carbon atoms; $R^7$ represents a lower alkyl group having 1 to 4 carbon atoms, a phenyl group or a carboxylalkyl group each of which may be substituted or a lower alkylsulfonyl group), $PO_3H_2$ or $SO_3H$, The compound of the present invention has an excellent antirheumatic function, psoriasis curing function and carcinostatic function and is also characterised in having a lower toxicity than that of the conventional methotrexate.

BRIEF DESCRIPTION OF THE DRAWINGS

FIG. 9 shows change in number of white blood cells (WBC) and red blood cells (RBC)

DESCRIPTION OF THE PREFERRED EMBODIMENTS

Figure 1:
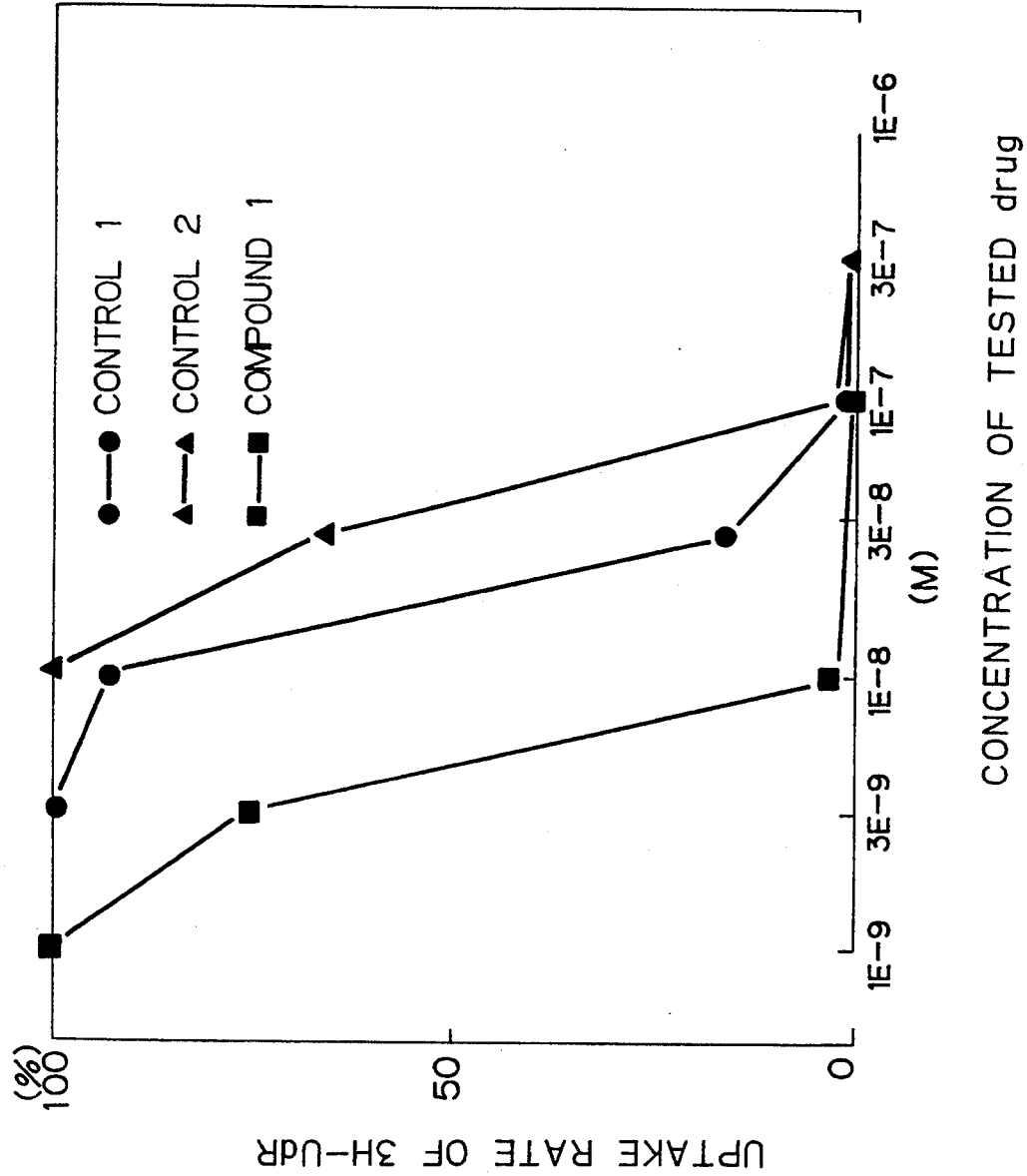
FIGS. 1 to 3 show amounts (ratio) of 3H-UdR to be uptake at a respective concentration of drugs to be tested.

The compounds of the present invention are each novel and have not yet been described in any of references and may be synthesized, for example, as follows:

Method A

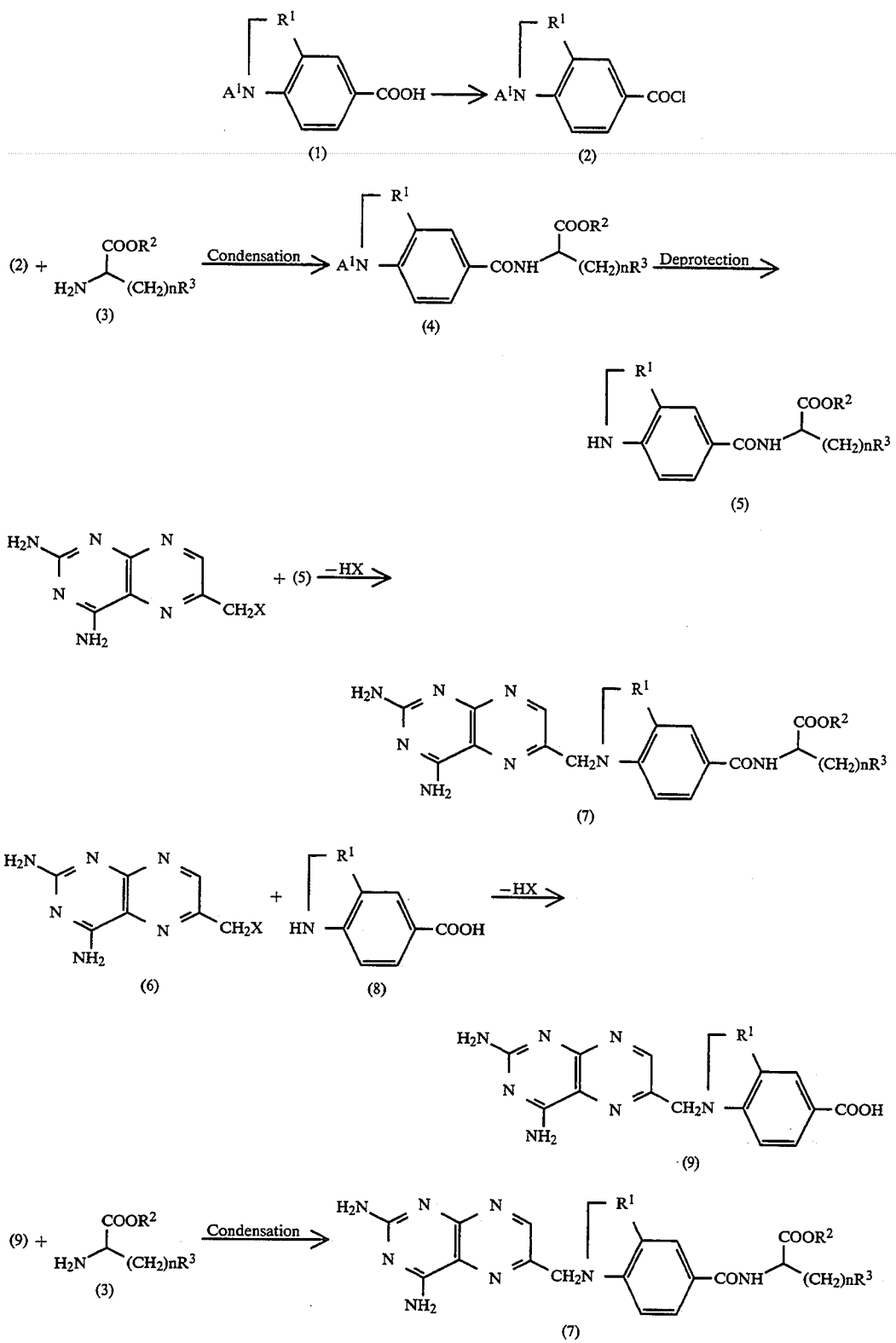
Method C
When $R_3$ in the formula (I) represents the formula:

wherein R' represents a hydrogen atom or a lower alkyl group having 1 to 4 carbon atoms, -continued

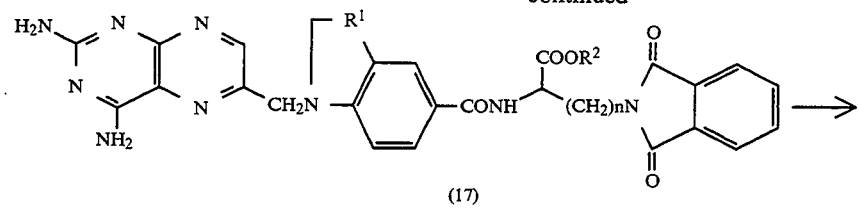

(17)

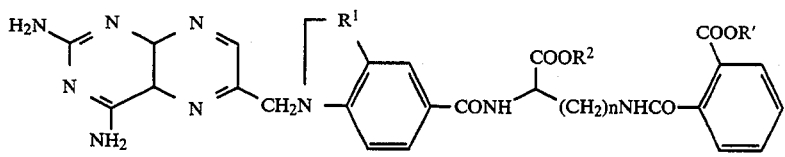

(18)

wherein $R^1$, $R^2$, $R^3$ and n have the same meanings as defined above, R' represents hydrogen atom or a lower alkyl group having 1 to 4 carbon atoms, $A^1$ and $A^2$ each represents a protective group and X represents a halogen atom.

In Method A, the reaction for obtaining the compound of the formula (2) from the compound of the formula (1) is carried out by suspending the compound of the formula (1) in an acid halogenating agent such as thionyl chloride, oxalyl chloride, etc. and stirring the mixture at room temperature in the co-presence of a catalytic amount of dimethylformamide, etc. In the formulae, as a protective group represented by $A^1$, there may be mentioned a carbobenzoxy group, a tosyl group, an acetyl group, etc.

The reaction for obtaining the compound of the formula (4) from the compound of the formula (2) and the compound of the formula (3) is carried out by adding a solution of the compound of the formula (2) dissolved in a solvent such as dichloromethane, etc. to an aqueous solution of the compound of the formula (3) under ice cooling or water cooling and then stirring the mixture at room temperature in the co-presence of an inorganic base such as potassium carbonate, sodium hydroxide, sodium hydrogen carbonate, etc.

The reaction for obtaining the compound of the formula (5) from the compound of the formula (4) is carried out by adding the compound of the formula (4) to a solution of anisol or phenol, etc. dissolved in a hydrobromide-acetic acid solution and stirring the mixture at 10° C. to 60° C., preferably at room temperature. Also, the reaction for obtaining the compound of the formula (5) from the compound of the formula (4) may be carried out by dissolving the compound of the formula (4) in a solvent such as methanol, ethanol, acetic acid, etc. and then stirring the mixture after adding palladium-carbon, under a hydrogen atmosphere at room temperature.

The reaction for obtaining the compound of the formula (7) from the compound of the formula (6) and the compound of the formula (5) is carried out by reacting the compound of the formula (6) and the compound of the formula (5) in a solvent such as dimethylacetamide, dimethylformamide, etc. at 0° C. to 100° C., preferably 50° C. to 60° C. under stirring. Particularly when $R^2$ is a hydrogen atom, 1N-sodium hydroxide aqueous solution is added to a solvent such as methanol, ethanol, etc. and stirring the mixture at 0° C. to 60° C., preferably at 35° C. to obtain the desired compound. In the formula, as the halogen atom represented by X, there may be mentioned a bromine atom, a chlorine atom, etc.

In Method B, the reaction for obtaining the compound of the formula (9) from the compound of the formula (6) and the compound of the formula (8) is carried out by reacting the compound of the formula (6) and the compound of the formula (8) in a solvent such as dimethylacetamide, dimethylformamide, etc. at 0° C. to 100° C., preferably 55° C. under stirring.

The reaction for obtaining the compound of the formula (7) from the compound of the formula (9) and the compound of the formula (3) is carried out by stirring the compound of the formula (9) in the co-presence of diethylphosphoric acid cyanide or dicyclohexylcarbodiimide and 1-hydroxybenzotriazole, etc. in a solvent such as dimethylformamide, dimethylacetamide, N-methylpyrrolidinone, etc., then adding the compound of the formula (3) and stirring the mixture at 0° C. to 200° C., preferably 10° C. to 80° C. under stirring. Particularly when $R^2$ is hydrogen atom, 1N-sodium hydroxide aqueous solution is added to the mixture and stirring the mixture at 0° C. to 60° C., preferably at room temperature to obtain the desired compound.

In Method C, the reaction for obtaining the compound of the formula (12) from the compound of the formula (10) and the compound of the formula (11) is carried out by dissolving the compound of the formula (10) in an aprotic solvent such as chloroform, dichloromethane, tetrahydrofuran, dioxane, etc., adding the compound of the formula (11), water and, for example, potassium carbonate, triethylamine, sodium hydrogen carbonate, pyridine, etc. to the mixture and stirring the mixture at room temperature. In the formulae, as a protective group represented by $A^2$, there may be mentioned a carbobenzoxy group, a tosyl group, an acetyl group, etc.

The reaction for obtaining the compound of the formula (13) from the compound of the formula (12) is carried out, in a solvent such as methanol, etc., by stirring at −60° C. to −20° C., preferably −30° C. and, after adding thionyl chloride, refluxing the mixture.

The reaction for obtaining the compound of the formula (14) from the compound of the formula (13) is carried out by dissolving the compound of the formula (13) in ethanol, methanol, tetrahydrofuran, dioxane, etc.

and stirring the mixture in the co-presence of palladium-carbon under hydrogen atmosphere at room temperature. The reaction for obtaining the compound of the formula (15) from the compound of the formula (14) and the compound of the formula (2) is carried out by dissolving the compound of the formula (2) in dichloromethane, etc., adding the compound of the formula (14) and potassium carbonate or triethylamine and water and stirring the mixture at room temperature, but amidation may be carried out by the mixed acid anhydride method, active ester or active amide method.

The reaction for obtaining the compound of the formula (16) from the compound of the formula (15) is carried out by adding hydrobromide-acetic acid to which anisol or phenol is previously dissolved therein to the compound of the formula (15) and stirring the mixture at room temperature.

The reaction for obtaining the compound of the formula (17) from the compound of the formula (6) and the compound of the formula (16) is carried out, after stirring in an aprotic solvent such as dimethylacetamide and dimethylformamide, etc. at 25° C. to 100° C., preferably 50° C. to 65° C., stirring the mixture in water containing, for example, triethylamine, potassium carbonate or sodium hydrogen carbonate, etc.

The reaction for obtaining the compound (I) from the compound of the formula (17) is carried out in a solvent such as ethanol, etc. by adding an aqueous sodium hydroxide solution and stirring the mixture at room temperature.

The compound represented by the formula (I) obtained according to the present invention has antirheumatic function, psoriasis curing function and carcinostatic function. Also, as compared with methotrexate, it has less toxicity. These functions are confirmed by examining the following experiments:

1. Growth inhibition function of human peripheral blood derived lymphocyte (antirheumatic function)
2. Growth inhibition experiment of rat and human keratinocytes (psoriasis curing function)
3. Mouse cancer cell growth inhibition experiment (carcinostatic function)
4. Toxicity comparison of methotrexate (MTX) and the compound of the present invention according to intraperitoneal continuous administration using rats.

Experimental Example 1

Growth inhibition function of human peripheral blood derived lymphocyte (antirheumatic function)

Method

Lymphocytes were separated from human peripheral blood by using Ficoll-Paque$^R$ and a drug suitably diluted and 105 lymphocytes were cultivated with PHA (0.3 μg/ml) in 96-hole culture plate for 2 days. Five hours before completion of the cultivation, $^3$H-UdR (1 μCi/well) was added and uptake of $^3$H-UdR in lymphocytes was measured by a scintillation counter (here, PHA shows phytohaemagglutinin and UdR deoxyuridine). Drugs used are as shown below.

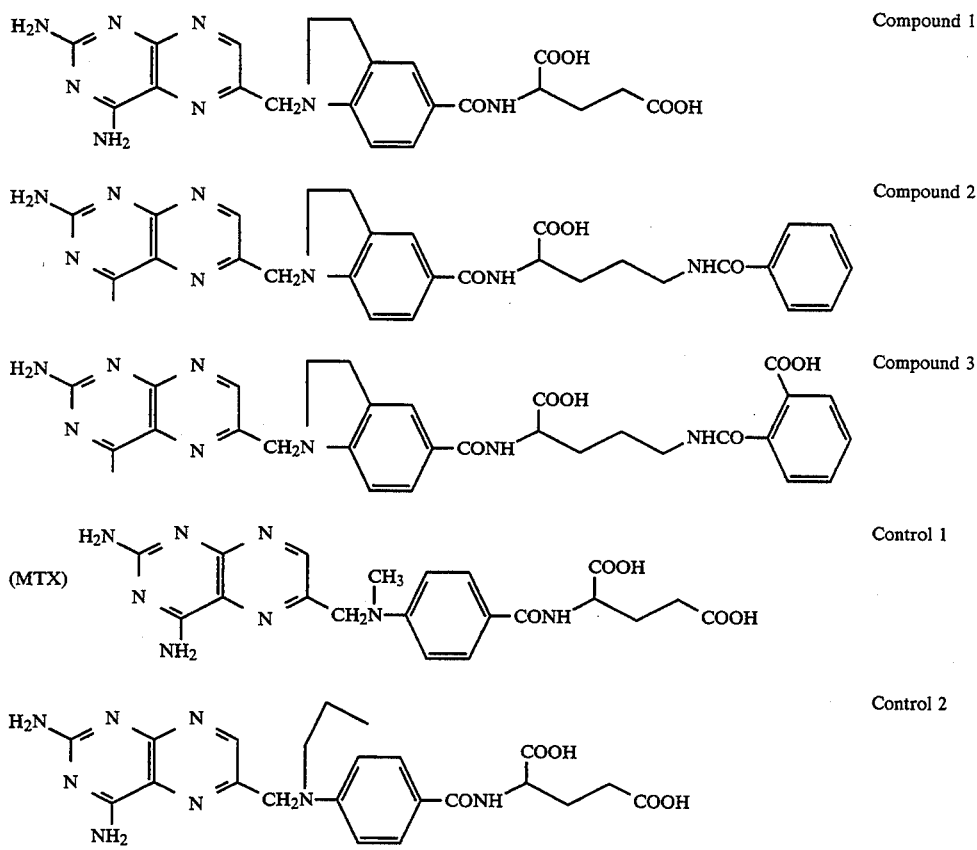

Results and Consideration

Figure 2:
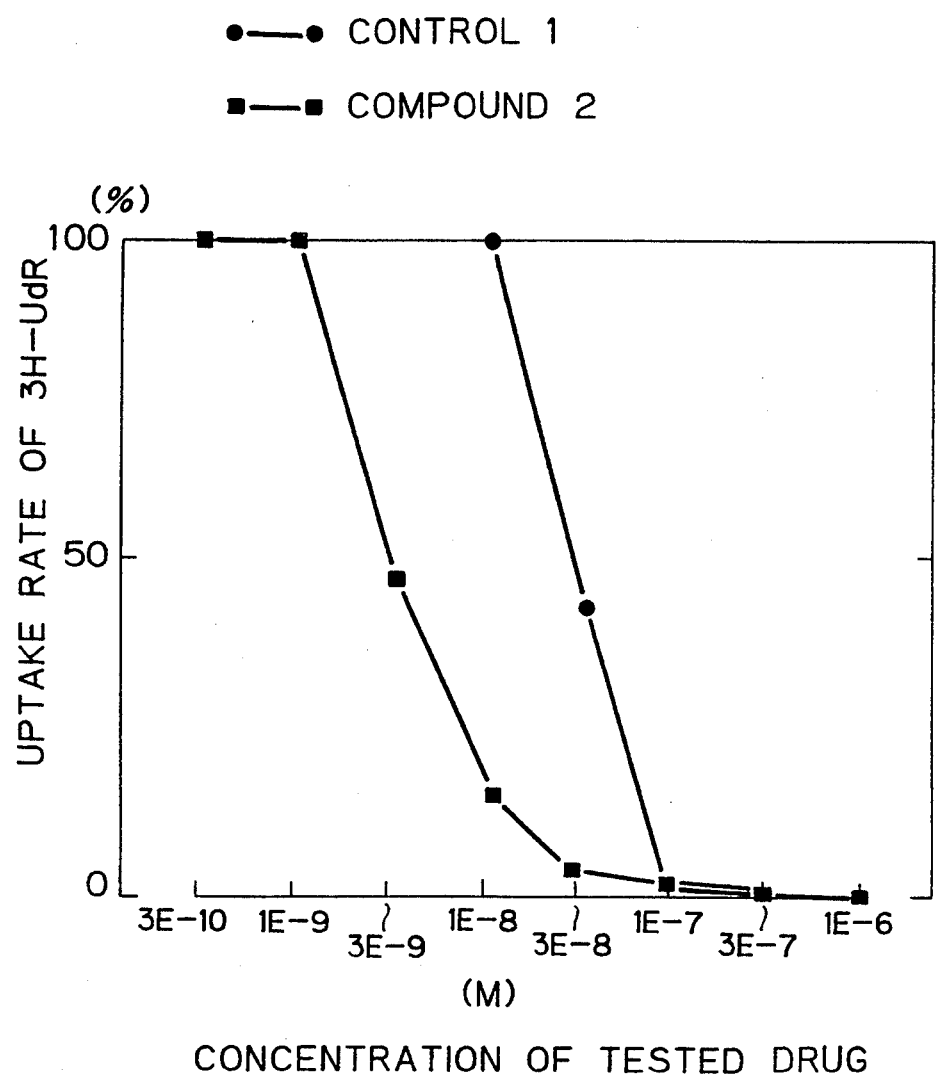
Figure 3:
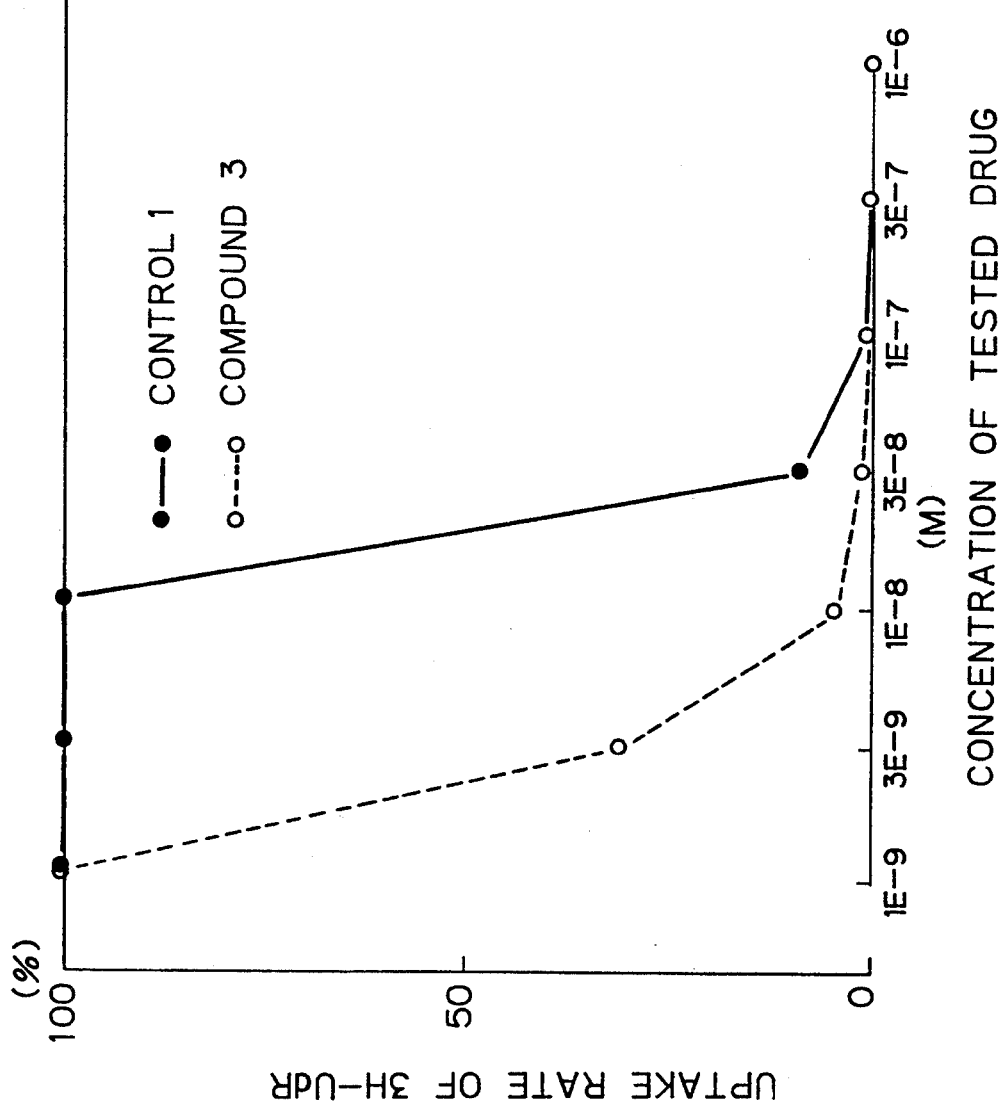

In FIGS. 1 to 3, ratios based on 3H-UdR uptake of PHA stimulus lymphocytes adding no drug as 100% are shown. As clearly seen from FIGS. 1 to 3, it was confirmed that the compounds of the present invention have excellent growth inhibition function of lymphocytes (antirheumatic function) than those of Control compounds.

Experimental Example 2

Growth inhibition experiment of rat and human keratinocytes (psoriasis curing function)

(1) Rat Keratinocyte Growth Inhibition Experiment

1) The first cultured rat keratinocyte by using Swiss 3T3 cell as a feeder layer was sewed with a concentration of $4 \times 10^4$ cells/ml/well to a 24-hole plate treated by Type IV collagen by using MCDB 153/DME/10% FCS medium containing growth factors (insulin, hydrocortisone, EGF, cholera toxin) and cultivated under 5% $CO_2$ and 95% Air at 37° C.

2) After 24 hours, it was washed twice at MCDB 153 medium containing no thymidine nor adenine and a medium exchange was carried out with MCDB 153 medium (1.8 mM Ca) containing growth factors (insulin, hydrocortisone, EGF, cholera toxin) and containing no thymidine nor adenine, and after adding a drug thereto, cultivation was carried out under 5% $CO_2$ and 95% Air at 37° C. for 4 days.

3) 0.5% MTT (3-(4,5-dimethylthiazol-2-yl)-2,5-diphenyltetrazolium bromide) was added with 100 μl/well and allowing to stand at 37° C. for 4 hours, and the medium was sucked up. Dye (formazan) formed by living cells was dissolved by adding DMSO (dimethylsulfoxide) with 200 μl/well. Absorbance (A 540) of the dye dissolved was measured and an average of 6-hole was calculated as a relative value of number of cells.

(2) Human Keratinocyte Growth Inhibition Experiment

1) Human keratinocyte obtained from Kurabou K.K. was sewed with a concentration of $2 \times 10^4$ cells/ml/well to a 24-hole plate treated by Type IV collagen by using MCDB 153 medium (0.15 mM Ca) containing growth factors (insulin, hydrocortisone, rhEGF, ethanolamine, phosphoethanolamine) and containing no thymidine nor adenine, and cultivated under 5% $CO_2$ and 95% Air at 37° C.

2) After 24 hours, a specimen was added thereto and the mixture was cultivated under 5% $CO_2$ and 95% Air at 37° C. for 4 days.

3) 0.5% MTT (3-(4,5-dimethylthiazol-2-yl)-2,5-diphenyltetrazolium bromide) was added with 100 μl/well and allowing to stand at 37° C. for 4 hours, and the medium was sucked up. Dye (formazan) formed by living cells was dissolved by adding DMSO (dimethylsulfoxide) with 200 μl/well. Absorbance (A 550) of the dye dissolved was measured and an average of 6-hole was calculated as a relative value of number of cells.

Drugs used are as shown below.

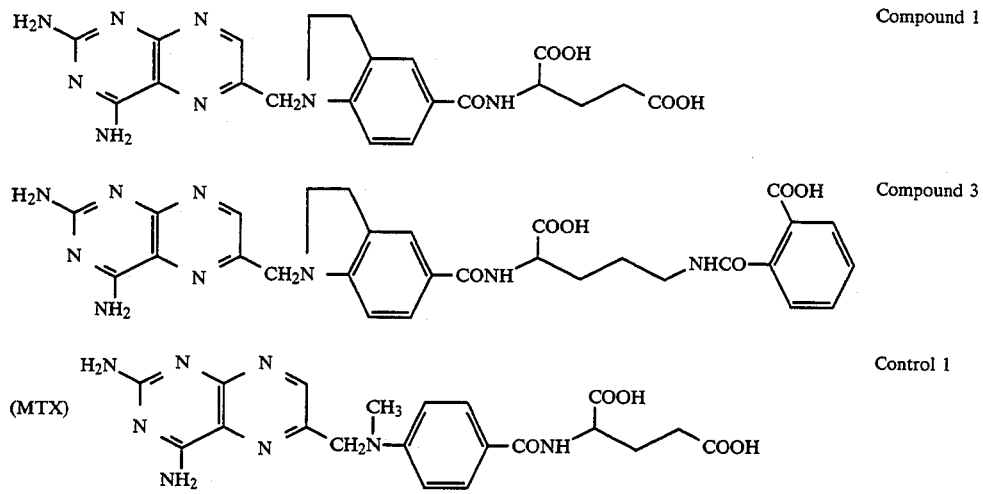

Compound 1

Compound 3

Control 1 (MTX)

Results and Consideration

Figure 4:
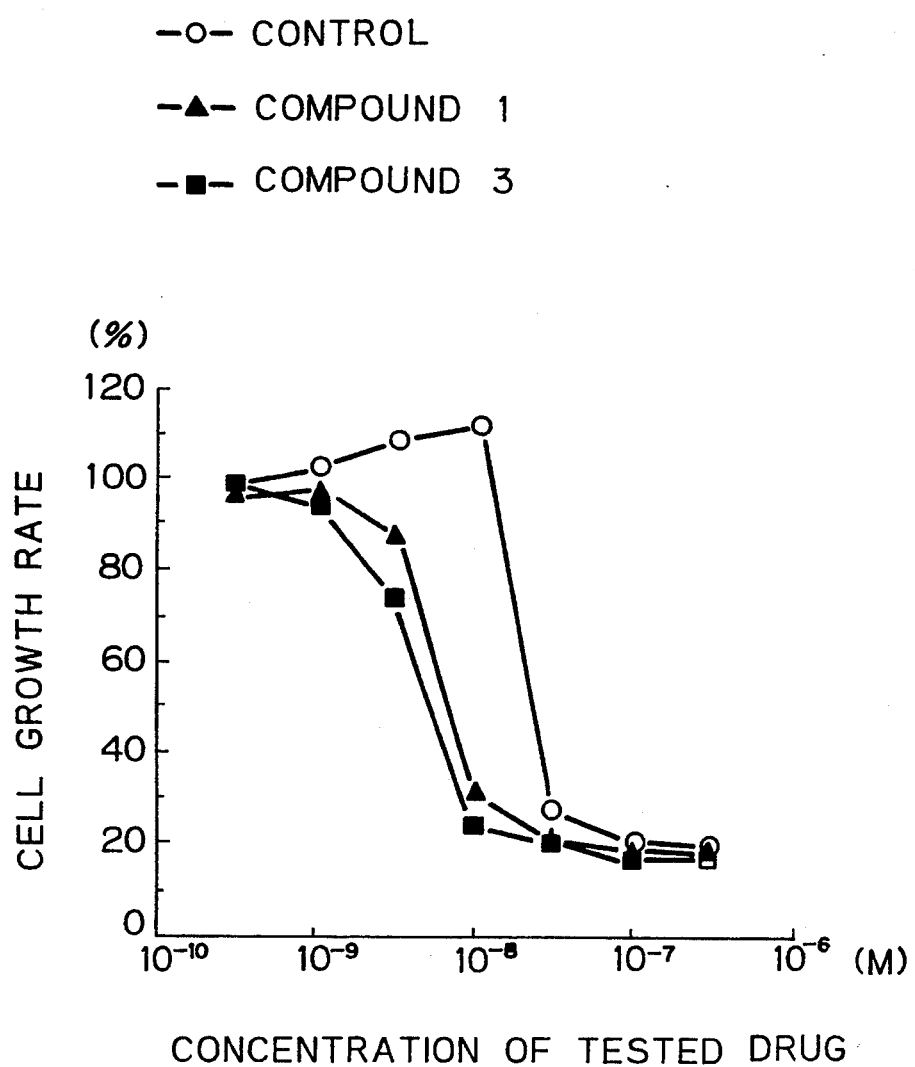
FIG. 4 shows "rat keratinocyte growth inhibitions function" and FIG. 5 shows "human keratinocyte growth inhibition function", respectively. Absorbances at respective concentrations of drugs to be tested are shown based on an absorbance when no drug is added as 100%.
Figure 5:
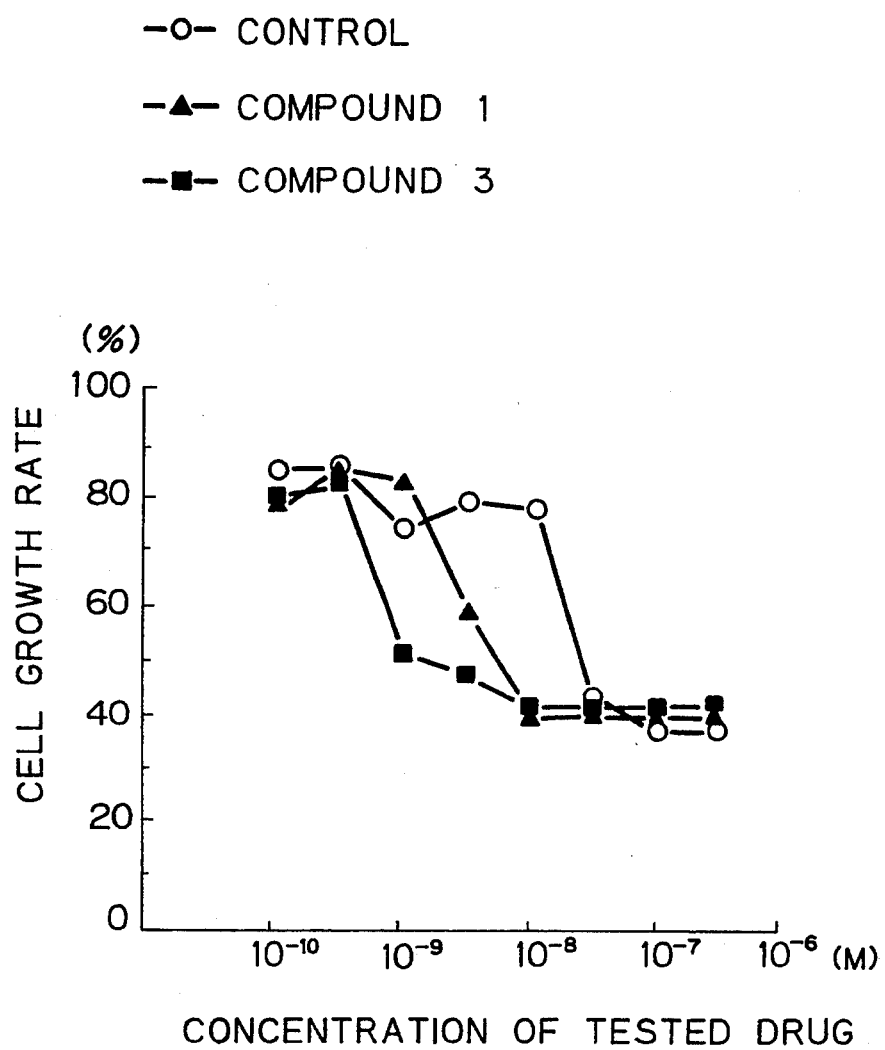

In FIG. 4, the results of "rat keratinocyte growth inhibition experiment" are shown and in FIG. 5, the results of "human keratinocyte growth inhibition experiment" are shown. Each is shown as a ratio based on the absorbance to which no drug is added as 100%.

As clearly seen from FIG. 4 and FIG. 5, it was confirmed that the compounds of the present invention have excellent keratinocyte growth inhibition function (psoriasis curing function) than that of Control compound.

Experimental Example 3

Mouse cancer cell growth inhibition experiment (carcinostatic function)

Method

Mouse lymphoid neoplasma P388 cell floated by RPM 11640 medium (added so as to have 5% of bovine fetal serum and $10^{-6}$M of 2-mercaptoethanol), or mouse colon 26 carcinoma cell were placed in each well of a flat-bottom microplate (available from Corning Co., #25870) with $5 \times 10^3$, and a drug solution prepared in the same medium was placed so as to have 0.2 ml of the drug in each well. These were cultivated in a carbonic gas cultivating device (carbonic gas 5%, air 95%, humidity 100%) for 3 days and then MTT solution (3-(4,5-dimethylthiazol-2-yl)-2,5-di-phenyltetrazolium bromide was dissolved in phosphate buffer physiological saline solution (pH 7.4, 4.10 mM) with an amount of 5 mg/ml) was added to each well with an amount of 10 μl, and cultivated for further 4 hours. Cultivation supernatant was removed each 150 μl and formed dye (formazan) was dissolved in DMSO (dimethylsulfoxide; 150 μl/well), and absorbance (540 nm) was measured by a spectrophotometer for microplate.

Drugs used are as shown below.

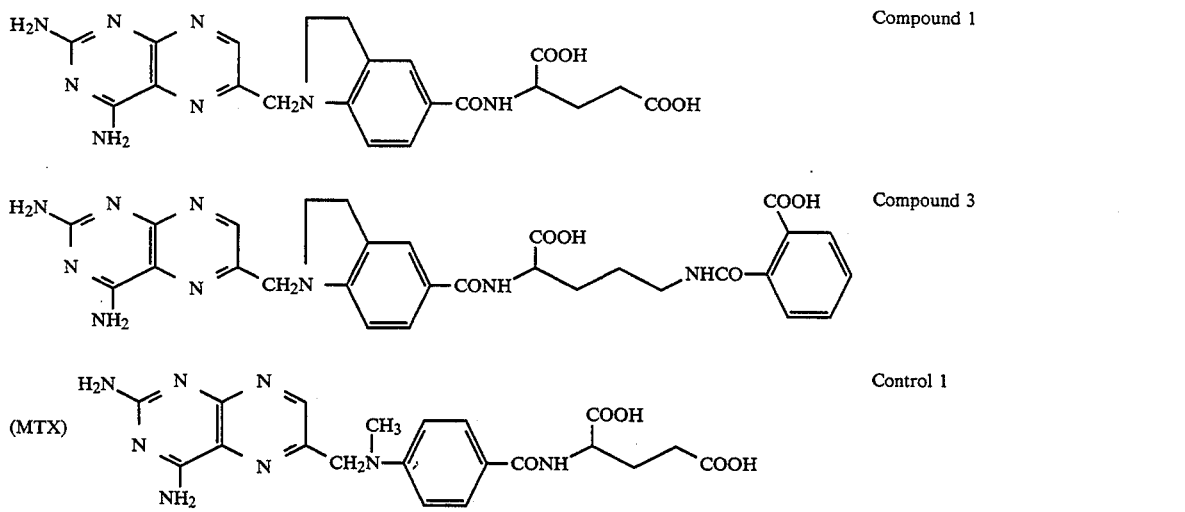

Results and Consideration

Figure 6:
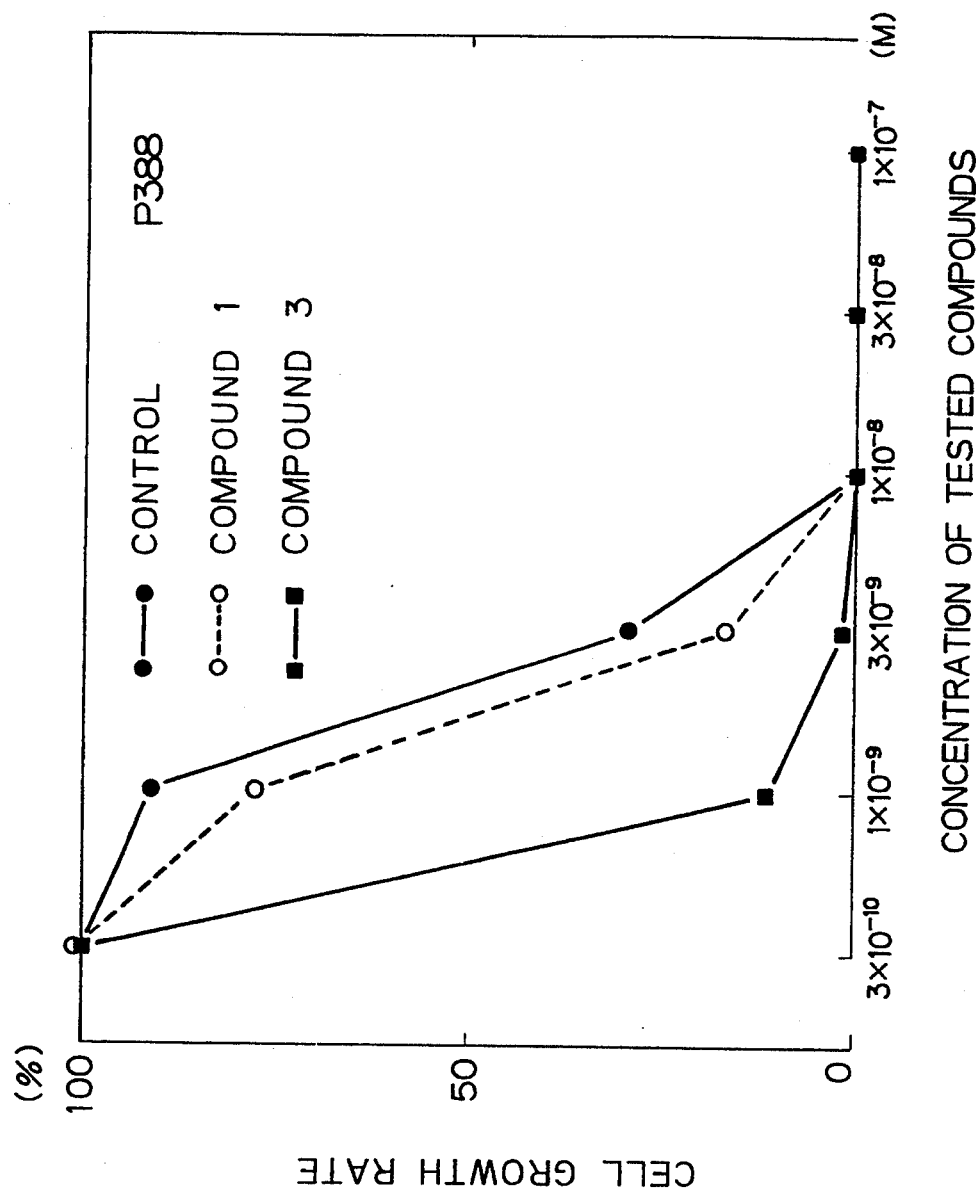
FIG. 6 shows "growth inhibition function of P388 cell" and FIG. 7 shows "growth inhibition function of colon 26". Absorbances at respective concentrations of drugs to be tested are shown based on an absorbance when no drug is added as 100%.
Figure 7:
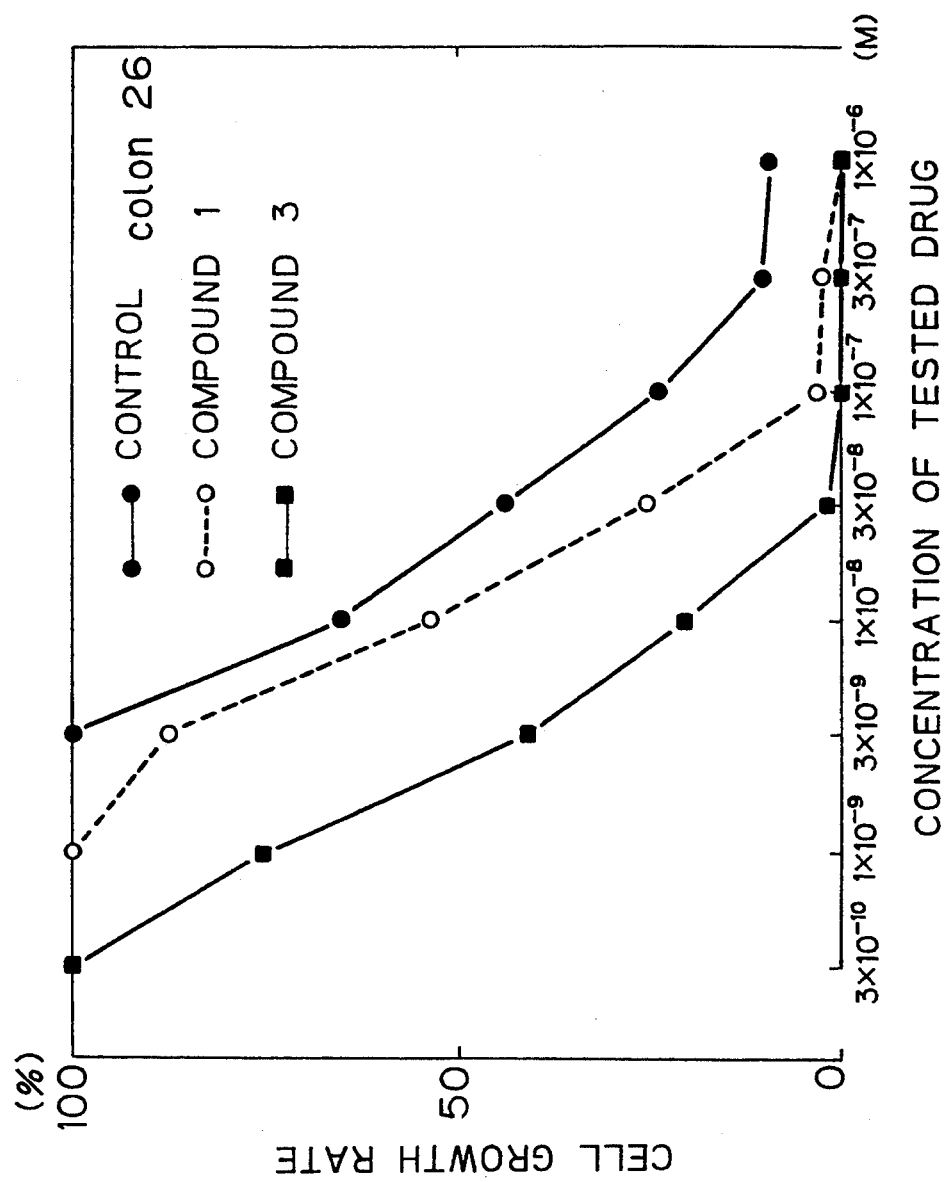

In FIG. 6, example of using P388 cell was shown and in FIG. 7, example of using colon 26 was shown. The data show with %, by cell growth at a well adding no drug, i.e. its absorbance as 100%, and the degree of inhibiting growth by addition of drugs.

As clearly seen from FIG. 6 and FIG. 7, it was con-

3) Blood inspection: at final week for administration, numbers of white blood cells (WBC) and red blood cells (RBC) were measured.
4) Liver weight and triglyceride (TG) content in liver: after final administration, anatomy was effected and liver weight and TG content in liver were measured.

Drugs used are as shown below.

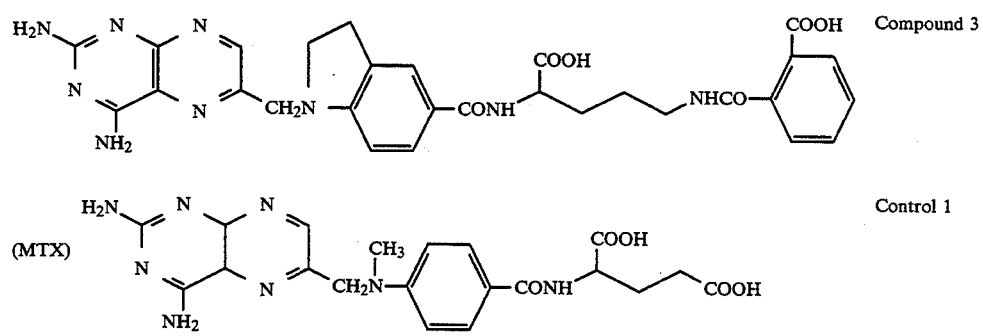

firmed that the compounds of the present invention have a far better cancer cell growth inhibition function (carcinostatic function) than that of Control drug.

Experimental Example 4

Toxicity comparison of methotrexate (MTX) and the compound of the present invention according to intraperitoneal continuous administration using rats

Method

To 8-week old SD series male rat was abdominary administered MTX or the compound of the present invention one per day with a ratio of 5 days per week for 5 weeks continuously. Doses administered are two degrees of 0.25 and 0.5 mg/kg in each of MTX and the compound of the present invention. For control group, a solvent (phosphate buffer, pH 7.4) was administered similarly. Number of rats constituting one group are five.

Inspected items are as follows.
1) Alive or dead and symptoms: observed every day.
2) Change in body weight: measured once per week.

Results

1) Alive or dead and symptoms

Among MTX administered groups, in a group administered with a dose of 0.25 mg/kg, no mouse died and abnormal symptoms were not observed. However, in a group administered with a dose of 0.5 mg/kg, bad nutriture, anemia, decrease in amount of dejection, swelling at mouse peripheral, etc. were observed and one of the five died.

On the other hand, in the group in which the compound of the present invention was administered, no mouse died in either 0.25 mg/kg group or 0.5 mg/kg group and no abnormal symptoms were observed.

2) Change in body weight

Figure 8:
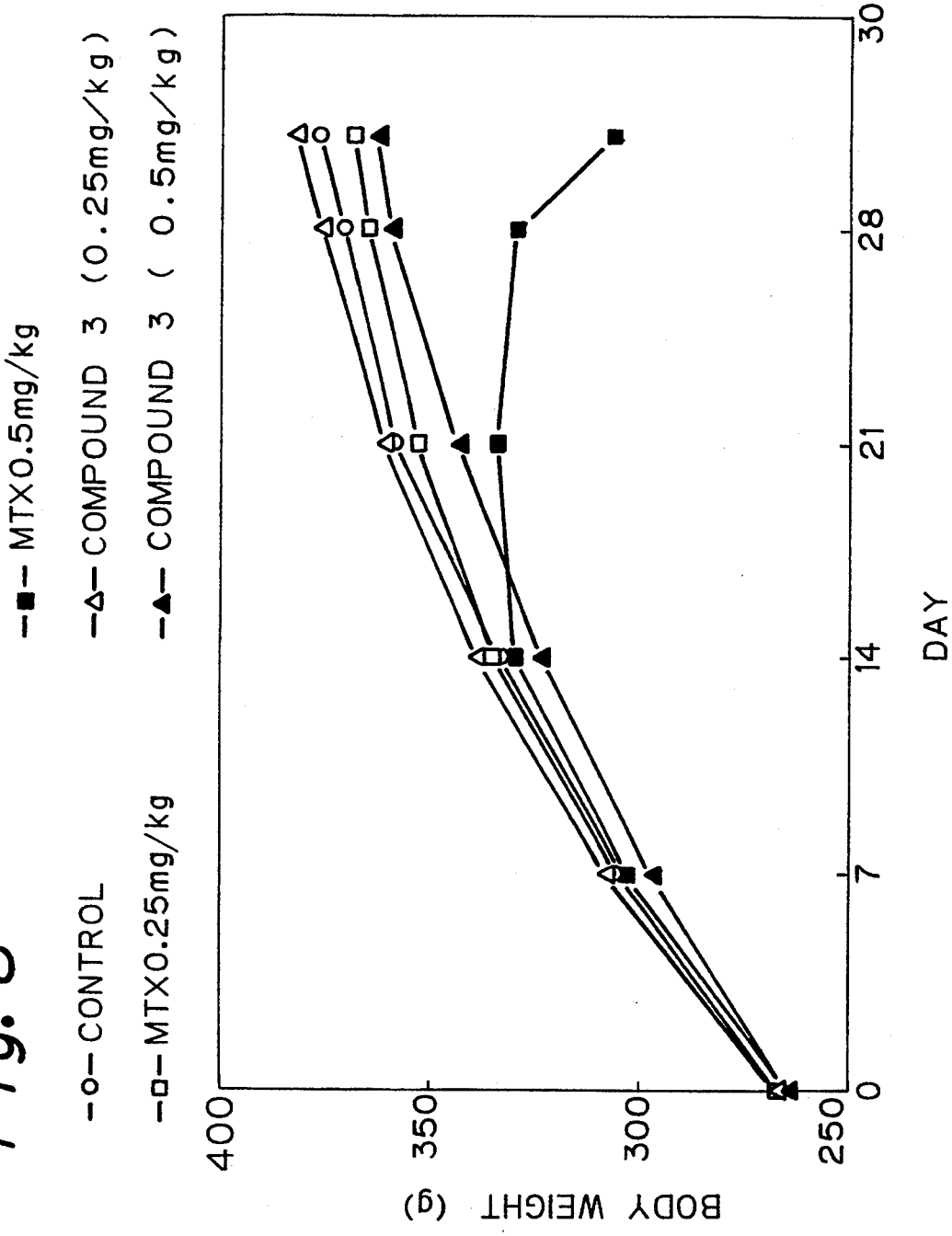
FIG. 8 shown weight changes in rats when methotrexate or the compound of the present invention is administered.

In FIG. 8, change in body weight is shown. Prohibition in body weight increment was weak in the compound of the present invention than that of MTX.

3) Blood inspection

In FIG. 9, the results of blood inspection are shown. Decrease in WBC and RBC are clearly weak in the compound of the present invention than that of MTX.

4) Liver weight and TG content in liver

Figure 10B:
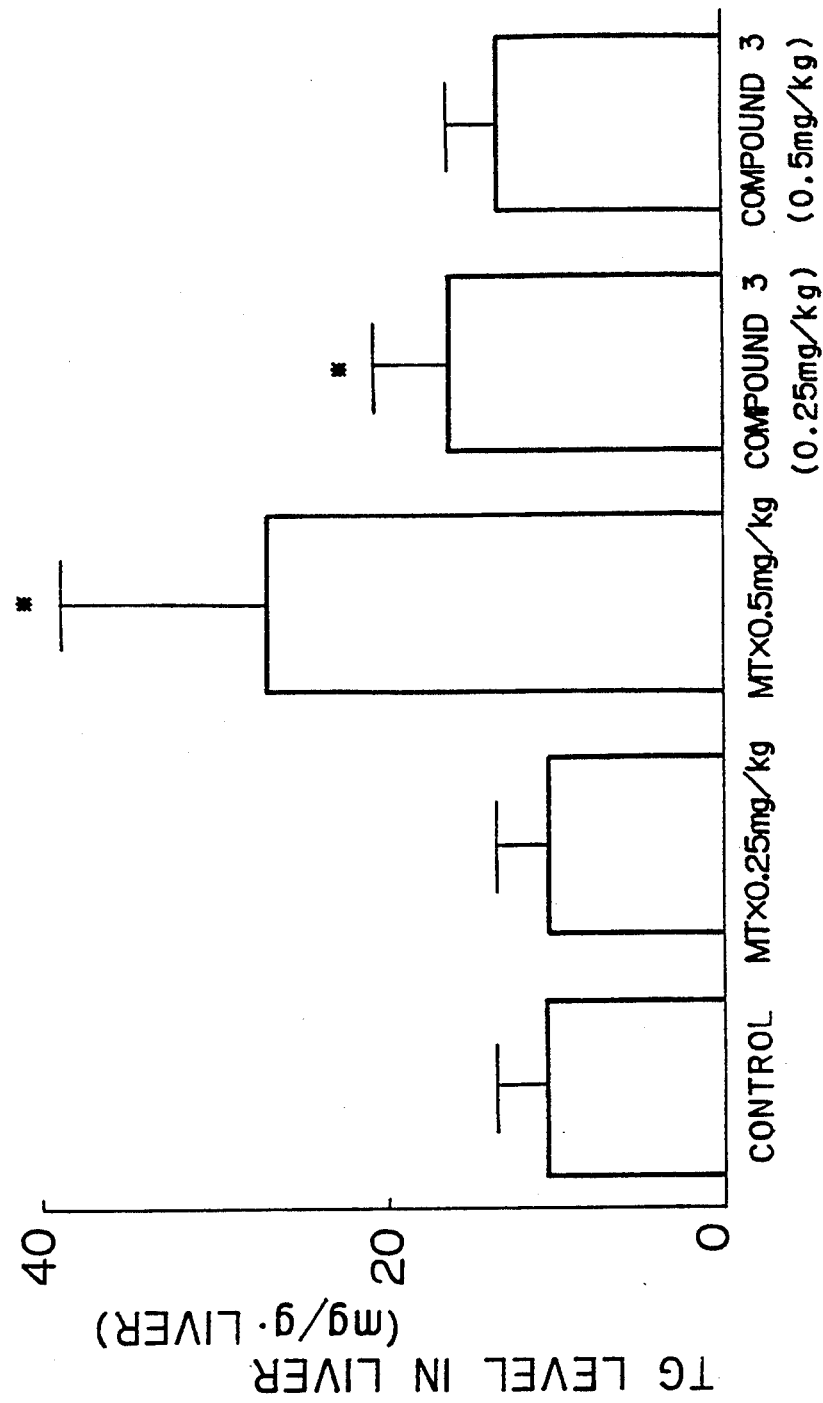
FIG. 10 shows changes in liver function and TG content in liver.

In FIG. 10, liver weight and TG content in liver are shown. Increment in liver weight and TG content in liver are both lower with the compound of the present invention than those of MTX.

Consideration

Toxicities of MTX and the compound of the present invention were compared by using rats due to abdominal continuous administration. As the results, in all of the points of the death ratio, symptom, body weight change, blood inspection, liver weight and TG content in liver, it can be considered to be low in toxicity of the compound of the present invention than those of MTX.

EXAMPLES

Reference Example 1

Synthesis of 1-carbobenzoxy-5-carboxyindoline

To a mixture of water (20 ml) and diethyl ether (20 ml) were added 5-carboxyindoline (2.0 g) and sodium hydroxide (0.6 g), and then, under ice-water cooling, carbobenzoxy chloride (2.59 g) and water (10 ml) containing sodium hydroxide (2.1 g) were added to the mixture thereto alternatively. The mixture was stirred at room temperature for 2 hours. The reaction mixture was made acidic with 2N-hydrochloric acid and precipitated crystals were collected by filtration. Precipitates were washed with ether and air-dried to obtain the title compound (2.8 g).

$^1$H-NMR (DMSO-$d_6$, δ): 3.10 (2H, t, J=8 Hz), 4.03 (2H, t, J=8 Hz), 5.23 (2H, s), 7.2–8.0 (8H, m). mp; 194°–196° C.

Reference Example 2

Synthesis of diethyl N-(1-carboxybenzoxyindolin-5-carbonyl)-L-glutamate

After suspending the compound (2.5 g) of Reference example 1 in thionyl chloride (10 ml), a catalytic amount of dimethylformamide was added to the mixture and the mixture was stirred at room temperature for 30 minutes. Then, excessive thionyl chloride was removed under reduced pressure and the residue was triturated by n-hexane. The resulting crystals were filtered and dissolved in dichloromethane (20 ml), and the dichloromethane solution was added dropwise to a water (50 ml) suspension containing diethyl glutamate hydrochloride (3.0 g) and triethylamine (2.8 g) under ice-water cooling. After stirring the mixture at room temperature for 2.5 hours, the solvent was removed under reduced pressure and to the residue was added a mixed solution of ethyl acetate (200 ml) and dil. hydrochloric acid (200 ml) under ice-water cooling. After stirring the mixture for 5 minutes, the organic layer was obtained by separation. The organic layer was washed with 5% aqueous sodium hydrogen carbonate solution and then dried over magnesium sulfate. Then, ethyl acetate was removed under reduced pressure, and the residue was subjected to silica gel column chromatography using a mixed solvent of chloroform:methanol=30:1 as an eluent to obtain the title compound (3.1 g).

$^1$H-NMR (CDCl$_3$, δ): 1.19 (3H, t, J=7 Hz), 1.25 (3H, t, J=7 Hz), 2.1–2.6 (4H, m), 3.06 (2H, t, J=8 Hz), 3.8–4.3 (6H, m) 4.75 (1H, m), 5.20 (2H, s), 6.79 (1H, d, J=7 Hz), 7.2–7.7 (8H, m). mp; 120°–121° C.

Reference Example 3

Synthesis of diethyl N-(indolin-5-carbonyl)-L-glutamate

The compound (1.8 g) of Reference example 2 was dissolved in tetrahydrofuran (80 ml), and after adding 10% palladium-carbon (0.4 g), the mixture was stirred under hydrogen atmosphere for 5 hours. Palladium-carbon was removed by filtration using Celite to obtain the title compound (1.2 g)

$^1$H-NMR (CDCl$_3$, δ): 1.21 (3H, t, J=7 Hz), 1.29 (3H, t, J=7 Hz), 2.0–2.6 (4H, m), 3.00 (2H, t, J=8 Hz), 3.59 (2H, t, J=8 Hz), 4.07 (2H, q, J=7 Hz), 4.19 (2H, q, J=7 Hz) 4.75 (1H, m), 6.47 (1H, d, J=9 Hz), 6.68 (1H, d, J=7 Hz), 7.45 (1H, d, J=9 Hz), 7.49 (1H, mp; 96°–97° C.

Example 1

Synthesis of diethyl N-[1-[(2,4-diamino-6-pteridinyl)methyl]indolin-5-carbonyl]-L-glutamate In dimethylacetamide (3 ml) were suspended the compound (214 mg) of Reference example 3 and 6-bromomethyl-2,4-diaminopteridine hydrobromate.isopropanol adduct (250 mg), and the mixture was stirred at 50°–55° C. for 4 hours. After cooling, water (15 ml) containing triethylamine (124 mg) was added to the reaction mixture, and then the mixture was extracted with chloroform (350 ml) dividing into four times. After the organic layer was dried over magnesium sulfate, the solvent was removed under reduced pressure and the residue subjected to silica gel column chromatography using a mixed solvent of chloroform:methanol=10:1 as an eluent to obtain the title compound (200 mg).

$^1$H-NMR (DMSO-$d_6$, δ): 1.22 (3H, t, J=7 Hz), 1.30 (3H, t, J=7 Hz), 2.0–2.5 (4H, m), 3.07 (2H, t, J=8 Hz), 3.57 (2H, t, J=8 Hz), 4.10 (2H, q, J=7 Hz), 4.23 (2H, q, J=7 Hz) 4.79 (1H, m), 5.24 (2H, s), 6.51 (1H, d, J=9 Hz), 6.76 (1H, d, J=7 Hz), 7.57 (1H, s), 7.59 (1H, d, J=9 Hz), 8.82 (1H, s). mp; 168°–170° C.

Example 2

Synthesis of N-[1-[(2,4-diamino-6-pteridinyl)methyl]indolin-5-carbonyl]-L-glutamic acid (Compound 1)

The compound (170 mg) of Example 1 was dissolved in ethanol (33 ml), and 1N aqueous sodium hydroxide solution (0.84 ml) was added to the solution at 35° C. and the mixture was stirred at the same temperature for 4.5 hours. After continuing stirring at 25° C. for further 20 hours, water (2 ml) was added to the reaction mixture. The reaction mixture was evaporated to dryness under reduced pressure. The residue obtained was dissolved in water (15 ml), and the solution was adjusted to pH=3.7 with 1N-hydrochloric acid under ice-water cooling and allowed to stand at cool place overnight. Deposited precipitates were collected by filtration to obtain the title compound (130 mg).

$^1$H-NMR (DMSO-$d_6$, δ): 1.94 (2H, m), 2.32 (2H, m), 2.98 (2H, t, J=8 Hz), 3.56 (2H, t, J=8 Hz), 4.29 (1H, m), 4.53 (2H, s), 6.71 (1H, d, J=9 Hz), 7.57 (1H, s), 7.59 (1H, d, J=9 Hz), 8.72 (1H, s). mp; 201°–204° C. (decomposed)

Reference Example 4

Synthesis of dimethyl N-(1-carbobenzoxyindolin-5-carbonyl)-L-α-aminoadipate

After suspending 1-carbobenzoxyindolin-5-carboxylic acid (3.1 g) in thionyl chloride (10 ml), a catalytic amount of dimethylformamide was added to the suspension and the mixture was stirred at room temperature for 2 hours. Then, excessive thionyl chloride was removed under reduced pressure and the residue was triturated by n-hexane. The resulting crystals were filtered and dissolved in dichloromethane (30 ml), and the dichloromethane solution was added dropwise to an aqueous solution (30 ml) containing dimethyl L-α-aminoadipate hydrochloride (2.7 g) under ice-water cooling. To the reaction solution was further added potassium carbonate (5.6 g). After stirring the mixture at room temperature overnight, the reaction mixture was poured into a saturated aqueous sodium hydrogen carbonate solution and extracted with chloroform. The chloroform layer was washed with 1N-hydrochloric acid and dried over sodium sulfate, and then the solvent was removed under reduced pressure. Then, the residue obtained was subjected to silica gel column chromatography using a mixed solvent of chloroform:methanol=100:1 as an eluent to obtain the title compound (3.1 g).

$^1$H-NMR (CDCl$_3$, δ): 1.6–2.1 (4H, m), 2.36 (2H, t, J=6.8 Hz), 3.13 (2H, m), 3.66 (3H, s), 3.77 (3H, s), 4.09 (2H, m), 4.78 (1H, m), 5.27 (2H, bs), 6.80 (1H, d, J=7.8 Hz), 7.2–7.5 (6H, m), 7.63 (2H, m).

Reference Example 5

Synthesis of dimethyl N-(indolin-5-carbonyl)-L-α-aminoadipate

To a 30% hydrogen bromide-acetic acid (15 ml) solution containing anisole (1.5 g) was added the compound (1.5 g) of Reference example 4 and the mixture was stirred at room temperature for 4 hours. Then, when a large amount of ether was added to the reaction mixture, a red-brownish oily product was precipitated. Almost all the ether layer was removed and the oily product was suspended in chloroform. The suspension was washed with a saturated aqueous sodium hydrogen carbonate solution and the chloroform layer was collected by separation. The chloroform layer was dried over sodium sulfate and the solvent was removed under reduced pressure to obtain the title compound (960 mg).

$^1$H-NMR (CDCl$_3$, δ): 1.6–2.1 (4H, m), 2.36 (2H, t, J=6.8 Hz), 3.07 (2H, m), 3.66 (3H, s), 3.66 (2H, m) 3.77 (2H, s), 4.78 (1H, m), 6.62 (2H, m), 7.54 (2H, m).

Example 3

Synthesis of dimethyl N-[1-[(2,4-diamino-6-pteridinyl)methyl]-indolin-5-carbonyl]-L-α-aminoadipate In dimethylacetamide (20 ml) were suspended the compound (960 mg) of Reference example 5 and 6-bromomethyl-2,4-diaminopteridine hydrobromide.isopropanol adduct (1140 mg) and the suspension was stirred at 50° to 60° C. for 6 hours. After cooling, the mixture was poured into a saturated aqueous sodium hydrogen carbonate solution, and the desired product was extracted with chloroform dividing into three times. The organic layer was dried over sodium sulfate and the solvent was removed under reduced pressure. The residue obtained was applied to silica gel column chromatography by using a mixed solvent of chloroform:methanol=100:10 as an eluent to obtain the title compound (520 mg).

$^1$H-NMR (CDCl$_3$, δ): 1.6–2.1 (4H, m), 2.38 (2H, t, J=6.8 Hz), 3.07 (2H, m), 3.57 (2H, m), 3.67 (3H, s) 3.78 (3H, s), 4.53 (2H, s), 4.74 (1H, m), 6.52 (1H, d, J=8.3 Hz), 7.01 (1H, d, J=7.8 Hz), 7.57 (2H, m), 8.77 (1H, s).

Example 4

Synthesis of N-[1-[(2,4-diamino-6-pteridinyl)methyl]-indolin-5-carbonyl]-L-α-aminoadipic acid The compound (400 mg) of Example 3 was dissolved in ethanol (22 ml), and 1N aqueous sodium hydroxide solution (3.1 ml) was added to the solution at 35° C. and the mixture was stirred at the same temperature for 4 hours. After continuing stirring at 25° C. for further 20 hours, water (3 ml) was added to the reaction mixture, and the reaction mixture was evaporated to dryness under reduced pressure. During this procedure, the outer temperature was controlled so as not to exceed 30° C. A yellowish solid material was obtained dissolved in water (10 ml), and the solution was adjusted to pH=3.7 with 1N-hydrochloric acid and allowed to stand in a refrigerator for 2 hours. Deposited precipitates were collected by filtration to obtain the title compound (320 mg).

$^1$H-NMR (CDCl$_3$, δ): 4–1.9 (4H, m), 2.23 (2H, t, J=6.8 Hz), 3.01 (2H, m), 3.58 (2H, m), 4.32 (1H, m), 4.55 (2H, s), 6.69 (1H, d, J=8.3 Hz), 7.63 (2H, m), 8.10 (1H, d, J=8.3 Hz), 8.72 (1H, s).

Reference Example 6

Synthesis of N$^α$-(1-carbobenzoxyindolin-5-carbonyl)-N$^δ$-benzoyl-L-ornithine methyl ester To thionyl chloride (1.5 ml) was added 1-carbobenzoxyindolin-5-carboxylic acid (180 mg) to make a suspension, and a catalytic amount of dimethylformamide was added to the suspension and the mixture was stirred at room temperature for 2 hours. Next, the mixture was evaporated to dryness under reduced pressure. The solid material obtained was dissolved in dichloromethane (4 ml), and to the solution were added N$^δ$-benzoyl-L-ornithine methyl ester (150 mg) and potassium carbonate (750 mg), and water (4 ml) was further added thereto and the mixture vigorously stirred at room temperature for 12 hours. Then, the reaction mixture was poured into water, extracted with chloroform and the chloroform layer was washed with a 1N-hydrochloric acid solution and dried over sodium sulfate. The solvent was removed under reduced pressure and the residue obtained was applied to silica gel chromatography by using chloroform:methanol=100:3 as an eluent to obtain the title compound (140 mg).

$^1$H-NMR (CDCl$_3$, δ): 1.6–2.2 (4H, m), 3.15 (2H, t, J=8.8 Hz), 3.56 (2H, m), 3.78 (3H, s), 4.10 (2H, t, J=8.8 Hz), 4.82 (1H, m), 5.27 (2H, s), 6.70 (1H, m), 6.89 (1H, d, J=8.8 Hz), 7.20 (8H, m), 7.80 (2H, m).

Reference Example 7

Synthesis of
$N^\alpha$-(indolin-5-carbonyl)-$N^\delta$-benzoyl-L-ornithine methyl ester The compound (140 mg) of Reference example 6 was added to a 30% hydrogen bromide-acetic acid (2 ml) of phenol (150 mg), and the mixture was stirred at room temperature for 4 hours. Next, when a large amount of ether was added to the reaction solution, red-brownish oily product was precipitated. Almost all the part of the ether layer was removed and the oily product was suspended in chloroform. The suspension was washed with a saturated aqueous sodium hydrogen carbonate solution and extracted with chloroform. The chloroform layer was dried over sodium sulfate and the solvent was removed under reduced pressure to obtain the title compound (50 mg).

$^1$H-NMR (CDCl$_3$, δ): 1.6–2.1 (4H, m), 3.02 (2H, t, J=8.8 Hz), 3.56 (2H, m), 3.62 (2H, t, J=8.8 Hz), 3.75 (3H, s), 4.79 (1H, m), 6.55 (1H, d, J=7.8 Hz), 6.86 (2H, m), 6.99 (1H, m), 7.1–7.6 (5H, m), 7.82 (2H, m).

Example 5

Synthesis of
$N^\alpha$-[1-[(2,4-diamino-6-pteridinyl)methyl]-indolin-5-carbonyl)-$N^\delta$-benzoyl-L-ornithine methyl ester In dimethylacetamide (1 ml) were suspended the compound (50 mg) of Reference example 7 and 6-bromomethyl-2,4-diaminopteridine hydrobromide.isopropanol adduct (44 mg), and the mixture was stirred at 50° to 55° C. for 4 hours. After cooling, water (3 ml) containing triethylamine (22 mg) was added to the reaction mixture, and then the mixture was extracted with chloroform. After the chloroform layer was dried over sodium sulfate, the solvent was removed under reduced pressure and the residue was applied to silica gel chromatography using a mixed solvent of chloroform:methanol=10:1 as an eluent to obtain the title compound (34 mg).

$^1$H-NMR (CDCl$_3$, δ): 1.6–2.2 (4H, m), 3.07 (2H, t, J=8.8 Hz), 3.50 (2H, m), 3.56 (2H, t, J=8.8 Hz), 3.79 (3H, s), 4.53 (2H, s), 4.76 (1H, s), 6.52 (1H, d, J=8.3 Hz), 7.19 (1H, d, J=7.6 Hz), 7.45 (3H, m), 7.62 (2H, m), 7.80 (2H, m), 8.76 (1H, s).

Example 6

Synthesis of
$N^\alpha$-[1-[(2,4-diamino-6-pteridinyl)methyl]-indolin-5-carbonyl)-$N^\delta$-benzoyl-L-ornithine In ethanol (5 ml) was dissolved the compound (34 mg) of Example 5, and 1N-sodium hydroxide aqueous solution (0.1 ml) was further added to the solution and the mixture was stirred at 35° C. for 4.5 hours. After stirring at 25° C. for 20 hours, water (1 ml) was added to the reaction mixture and the reaction mixture was evaporated to dryness under reduced pressure. During this procedure, the outer temperature was controlled so as not to exceed 30° C. A yellowish solid material was obtained and dissolved in water (5 ml), and the solution was adjusted to pH=3.7 with 1N-hydrochloric acid and allowed to stand in a refrigerator for 2 hours. Deposited precipitates were collected by filtration to obtain the title compound (26 mg).

$^1$H-NMR (DMSO-d$_6$, δ): 1.64 (2H, m), 1.83 (2H, m), 2.98 (2H, t, J=8.3 Hz), 3.57 (2H, t, J=8.3 Hz), 4.36 (1H, m), 4.53 (2H, s), 6.64 (2H, m), 7.45 (3H, m), 7.59 (2H, m), 7.82 (2H, m), 8.12 (1H, d, J=8.6 Hz), 8.43 (1H, m), 8.69 (1H, s). mp; 179°–183° C. (decomposed)

Reference Example 8

Synthesis of $N^\delta$-phthaloyl-$N^\alpha$-carbobenzoxy-ornithine methyl ester Phthalic anhydride (2.45 g) was added to a dichloromethane (70 ml) solution of $N^\alpha$-carbobenzoxy-L-ornithine (2.0 g), and then water (70 ml) and potassium carbonate (1.12 g) were added to the mixture and the mixture was stirred at room temperature for 15 hours. The mixture was condensed to 60 ml under reduced pressure and adjusted to pH=3 with 1N-hydrochloric acid. Deposited precipitates were collected by filtration and vacuum dried. White crystals obtained were dissolved in low water-content methanol (80 ml) and the solution was cooled to −30° C. and stirred for 10 minutes. Then, at the same temperature, thionyl chloride (2 ml) was slowly added dropwise. The reaction mixture was slowly returned to room temperature and reflexed for a further 2 hours. The solvent was removed under reduced pressure and the residue obtained was applied to silica gel chromatography by using chloroform:methanol=100:1 as an eluent to obtain the title compound (2.16 g).

$^1$H-NMR (CDCl$_3$, δ): 1.6–2.0 (4H, m), 3.69 (5H, m), 4.20 (1H, m), 5.06 (2H, s), 5.70 (1H, m), 7.29 (5H, m), 7.66 (2H, m), 7.81 (2H, m).

Reference Example 9

Synthesis of $N^\delta$-phthaloyl-ornithine methyl ester

After adding a 10% palladium-carbon (500 mg) to a methanol solution (100 ml) of the compound (2.16 g) of Reference example 8, the mixture was stirred under hydrogen atmosphere at room temperature for 20 hours. Palladium-carbon was removed by filtration using Celite and the solvent was removed under reduced pressure. The residue obtained was subjected to silica gel chromatography by using chloroform:methanol=100:3 as an eluent to obtain the title compound (223 mg).

$^1$H-NMR (CDCl$_3$, δ): 1.7–2.1 (4H, m), 3.75 (2H, m), 3.83 (3H, s), 7.76 (2H, m), 7.84 (2H, m).

Reference Example 10

Synthesis of
$N^\alpha$-(1-carbobenzoxyindolin-5-carbonyl)-$N^\delta$-phthaloyl-ornithine methyl ester By adding thionyl chloride (2.5 ml) to 1-carbobenzoxyindolin-5-carboxylic acid (297 mg) to prepare suspension, and a catalytic amount of dimethylformamide was added to the suspension and the mixture was stirred at room temperature for 2 hours. Then, the mixture was evaporated to dryness under reduced pressure. The resulting solid material was dissolved in dichloromethane (7 ml), and to the solution were added the compound (250 mg) of Reference example 9 and potassium carbonate (640 mg). Then, water (7 ml) was further added thereto, and the mixture was vigorously stirred at room temperature for 12 hours. Next, the reaction mixture was poured into water and extracted with chloroform, and the chloroform layer was washed with 1N-hydrochloric acid and dried over sodium sulfate. The solvent was removed under reduced pressure. The residue obtained was subjected to silica gel chromatography using chloroform:methanol=100:3 as an eluent to obtain the title compound (330 mg).

$^1$H-NMR (CDCl$_3$, δ): 1.6–2.1 (4H, m), 3.12 (2H, t, J=8.8 Hz), 3.72 (2H, m), 3.76 (3H, s), 4.08 (2H, t, J=8.8 Hz), 4.84 (1H, m), 5.27 (2H, s), 6.80 (1H, d, J=7.8 Hz), 7.1–7.5 (6H, m), 7.5–7.9 (6H, m).

Reference Example 11

Synthesis of N$^α$-(indolin-5-carbonyl)-N$^δ$-phthaloyl-ornithine methyl ester

To a 30% hydrogen bromide-acetic acid (8 ml) solution of phenol (300 mg) was added the compound (330 mg) of Reference example 10 and the mixture was stirred at room temperature for 4 hours. Then, when a large amount of ether was added to the reaction mixture, a red-brownish oily product was precipitated. Almost all the ether layer was removed and the oily product was suspended in chloroform. The suspension was washed with a saturated aqueous sodium hydrogen carbonate solution and extracted with chloroform. The chloroform layer was dried over sodium sulfate and the solvent was removed under reduced pressure to obtain the title compound (147 mg).

$^1$H-NMR (CDCl$_3$, δ): 1.6–2.1 (4H, m), 3.04 (2H, t, J=8.3 Hz), 3.62 (2H, t, J=8.3 Hz), 3.72 (2H, m), 3.75 (3H, s), 4.86 (1H, m), 6.5–6.7 (2H, m), 7.52 (2H, m), 7.68 (2H, m), 7.82 (2H, m).

Example 7

Synthesis of N$^α$-[1-[(2,4-diamino-6-pteridinyl)methyl]-indolin-5-carbonyl)-N$^δ$-phthaloyl-ornithine methyl ester In dimethylacetamide (1.0 ml) were suspended the compound (146 mg) of Reference example 11 and 6-bromomethyl-2,4-diaminopteridine hydrobromide·isopropanol adduct (115 mg) and the suspension was stirred at 50° to 55° C. for 4 hours. After cooling, to the mixture was added water (4 ml) containing triethylamine (30 mg), and the mixture was stirred and then extracted with chloroform. The chloroform layer was dried over sodium sulfate and the solvent was removed under reduced pressure. The residue obtained was applied to silica gel chromatography by using a mixed solvent of chloroform:methanol=10:1 as an eluent to obtain the title compound (140 mg).

$^1$H-NMR (CDCl$_3$, δ): 1.7–2.2 (4H, m), 3.06 (2H, t, J=8.3 Hz), 3.56 (2H, t, J=8.3 Hz), 3.72 (2H, m), 3.76 (3H, s), 4.53 (2H, s), 4.88 (1H, m), 6.45–6.62 (2H, m), 7.56 (2H, m), 7.71 (2H, m), 7.84 (2H, m), 8.82 (1H, s).

Example 8

Synthesis of N$^α$-[1-[(2,4-diamino-6-pteridinyl)methyl]-indolin-5-carbonyl)-N$^δ$-hemiphthaloyl-ornithine (Compound 3)

The compound (140 mg) of Example 7 was suspended in 2N-sodium hydroxide aqueous solution (10 ml), and the mixture was stirred at 30° C. for 12 hours. The mixture was evaporated to dryness under reduced pressure and yellowish solid material obtained was dissolved in water (5 ml). The solution was adjusted to pH=3.7 with 1N-hydrochloric acid and allowed to stand in a refrigerator for 2 hours. Deposited precipitates were collected by filtration. A yellowish solid material was obtained subjected to silica gel chromatography by using a mixed solvent of chloroform:methanol:28%-aqueous ammonia=5:4:1 as an eluent to obtain the title compound (20 mg).

$^1$H-NMR (DMSO-d$_6$, δ): 1.5–2.1 (4H, m), 3.14 (2H, t, J=8.3 Hz), 3.58 (2H, t, J=8.3 Hz), 4.38 (1H, m), 4.54 (2H, s), 6.71 (1H, m), 7.3–7.6 (4H, m), 7.6–7.8 (3H, m), 8.08 (1H, m), 8.71 (1H, s). mp; 195°–199° C. (decomposed)

Reference Example 12

Synthesis of N$^δ$-(3-methoxycarbonylbenzoyl)-N$^α$-carbobenzoxy-ornithine methyl ester To a dichloromethane (40 ml) solution of N$^α$-carbobenzoxy-L-ornithine (2.4 g) was added methyl isophthalate chloride (2.1 g), and then, water (40 ml) and potassium carbonate (2.4 g) were added to the mixture and the mixture was stirred at room temperature for 15 hours. The mixture was condensed under reduced pressure to 30 ml and adjusted to pH=3 with 1N-hydrochloric acid, and deposited precipitates were collected by filtration and vacuum dried. A white solid was obtained and dissolved in a low water-content methanol (100 ml) and the solution was cooled to −30° C. and stirred for 10 minutes. Then, thionyl chloride (3 ml) was gradually added dropwise at the same temperature. The reaction solution was slowly returned to room temperature and refluxed for a further 2 hours. The solvent was removed under reduced pressure and the residue obtained was subjected to silica gel chromatography by using chloroform:methanol=100:1 as an eluent to obtain the title compound (600 mg).

$^1$H-NMR (CDCl$_3$, δ): 1.6–2.0 (4H, m), 3.46 (2H, m), 3.70 (3H, s), 3.89 (3H, s), 4.34 (1H, m), 5.08 (2H, s), 5.88 (1H, d, J=7.8 Hz), 7.31 (5H, s), 7.45 (1H, m), 8.05 (2H, m), 8.41 (1H, s).

Reference Example 13

Synthesis of N$^δ$-(3-methoxycarbonylbenzoyl)-ornithine methyl ester

After adding a 10% palladium-carbon (100 mg) to a methanol solution (100 ml) of the compound (600 mg) of Reference example 12, the mixture was stirred under a hydrogen atmosphere at room temperature for 20 hours. Palladium-carbon was removed by filtration using Celite and the solvent was removed under reduced pressure. The residue obtained was subjected to silica gel chromatography by using chloroform:methanol=100:3 as an eluent to obtain the title compound (360 mg).

$^1$H-NMR (CDCl$_3$, δ): 1.6–2.0 (4H, m), 3.50 (3H, m), 3.72 (3H, s), 3.92 (3H, s), 7.49 (1H, t, J=7.8 Hz), 7.63 (1H, m), 8.0–8.2 (2H, m), 8.43 (1H, s).

Reference Example 14

Synthesis of N$^α$-(1-carbobenzoxyindolin-5-carbonyl)-N$^δ$-(3-methoxycarbonylbenzoyl)-ornithine methyl ester By adding thionyl chloride (5 ml) to 1-carbobenzoxyindolin-5-carboxylic acid (350 mg) to prepare suspension, and a catalytic amount of dimethylformamide was further added to the suspension and the mixture was stirred at room temperature for 2 hours. Then, the mixture was evaporated to dryness under reduced pressure. The resulting solid material was dissolved in dichloromethane (7 ml), and to the solution were added the compound (360 mg) of Reference example 13 and potassium carbonate (650 mg). Then, water (7 ml) was further added thereto, and the mixture was vigorously stirred at room temperature for 12 hours. Next, the reaction mixture was poured into water and extracted with chloroform, and the chloroform layer was washed with 1N-hydrochloric acid and dried over sodium sulfate. The solvent was removed under reduced pressure. The residue obtained was subjected to silica gel chromatography using chloroform:methanol=100:3 as an eluent to obtain the title compound (390 mg).

$^1$H-NMR (CDCl$_3$, δ): 1.6–2.1 (4H, m), 3.08 (2H, t, J=8.3 Hz), 3.52 (2H, m), 3.75 (3H, s), 3.88 (3H, s), 4.06 (2H, t, J=8.3 Hz), 4.78 (1H, m), 5.26 (2H, bs), 7.16 (1H, d, J=7.3 Hz), 7.2–7.6 (7H, m), 7.65 (2H, m), 7.9–8.1 (2H, m), 8.43 (1H, s).

Reference example 15

Synthesis of
N$^\alpha$-(indolin-5-carbonyl)-N$^\delta$-(3-methoxycarbonylbenzoyl)-ornithine methyl ester To a 30% hydrogen bromide-acetic acid (6 ml) solution of anisol (0.5 g) was added the compound (390 mg) of Reference example 14 and the mixture was stirred at room temperature for 4 hours. Then, when a large amount of ether was added to the reaction mixture, a red-brownish oily product was precipitated. Almost all the ether layer was removed and the oily product was suspended in chloroform. The suspension was washed with a saturated aqueous sodium hydrogen carbonate solution and extracted with chloroform. The chloroform layer was dried over sodium sulfate and the solvent was removed under reduced pressure. White solid obtained was recrystallized from n-hexane-chloroform-methanol to obtain the title compound (192 mg).

$^1$H-NMR (CDCl$_3$, δ): 1.7–2.1 (4H, m), 3.05 (2H, t, J=8.3 Hz), 3.53 (2H, m), 3.67 (2H, t, J=8.3 Hz), 3.75 (3H, s), 3.89 (3H, s), 4.75 (1H, m), 6.73 (1H, d, J=7.8 Hz), 7.16 (1H, d, J=7.8 Hz), 7.47 (1H, m), 7.55 (2H, m), 8.09 (2H, m), 8.45 (1H, s).

Example 9

Synthesis of
N$^\alpha$-[1-[(2,4-diamino-6-pteridinyl)methyl]-indolin-5-carbonyl)-N$^\delta$-(3-methoxycarbonylbenzoyl)-ornithine methyl ester In dimethylacetamide (2.5 ml) were suspended the compound (192 mg) of Reference example 15 and 6-bromomethyl-2,4-diaminopteridine hydrobromide (142 mg) and the suspension was stirred at 50° to 55° C. for 4 hours. After cooling, to the mixture was added water (5 ml) containing triethylamine (43 mg), and the mixture was stirred and then extracted with chloroform. The chloroform layer was dried over sodium sulfate and the solvent was removed under reduced pressure. The residue obtained was applied to silica gel chromatography by using a mixed solvent of chloroform:methanol=10:1 as an eluent to obtain the title compound (110 mg).

$^1$H-NMR (CDCl$_3$, δ): 1.7–2.1 (4H, m), 3.06 (2H, t, J=8.3 Hz), 3.55 (4H, m), 3.78 (3H, s), 3.93 (3H, s), 4.52 (2H, s), 4.79 (1H, m), 6.51 (1H, d, J=7.8 Hz), 7.05 (1H, d, J=7.8 Hz), 7.4–7.7 (3H, m), 8.0–8.2 (2H, m), 8.45 (1H, m), 8.77 (1H, s).

Example 10

Synthesis of
N$^\alpha$-[1-[(2,4-diamino-6-pteridinyl)methyl]-indolin-5-carbonyl)-N$^\delta$-isophthaloyl-ornithine The compound (110 mg) of Example 9 was dissolved in ethanol (14 ml), and 1N-sodium hydroxide aqueous solution (0.48 ml) was further added to the solution and the mixture was stirred at 35° C. for 4.5 hours. After the mixture was stirred at 25° C. for 20 hours, water (1 ml) was added to the reaction mixture and the reaction mixture was evaporated to dryness under reduced pressure. During this procedure, outer temperature was so controlled not to exceeding 30° C. A yellowish solid material was obtained and dissolved in water (5 ml), and the solution was adjusted to pH=3.7 with 1N-hydrochloric acid and allowed to stand in a refrigerator for 2 hours. Deposited precipitates were collected by filtration to obtain the title compound (78 mg).

$^1$H-NMR (DMSO-d$_6$, δ): 1.5–2.0 (4H, m), 3.00 (2H, t, J=8.8 Hz), 3.32 (2H, m), 3.59 (2H, t, J=8.8 Hz), 4.40 (1H, m), 4.56 (2H, s), 6.69 (1H, d, J=8.3 Hz), 7.56 (1H, m), 7.63 (2H, m), 8.0–8.2 (2H, m), 8.44 (1H, s), 8.65 (1H, m), 8.73 (1H, s).

Reference Example 16

Synthesis of
N$^\delta$-(4-methoxycarbonylbenzoyl)-N$^\alpha$-carbobenzoxy-ornithine methyl ester To a dichloromethane (60 ml) solution of N$^\alpha$-carbobenzoxy-L-ornithine (2.0 g) was added methyl terephthalate chloride (3.0 g), and then, water (60 ml) and potassium carbonate (4.8 g) were added to the mixture and the mixture was stirred at room temperature for 15 hours. The mixture was condensed under reduced pressure to 50 ml and adjusted to pH=3 with 1N-hydrochloric acid, and deposited precipitates were collected by filtration and vacuum dried. White solid obtained was dissolved in a low water-content methanol (100 ml) and the solution was cooled to −30° C. and stirred for 10 minutes. Then, thionyl chloride (3 ml) was gradually added dropwise at the same temperature. The reaction solution was slowly returned to room temperature and refluxed for further 2 hours. The solvent was removed under reduced pressure and the residue obtained was subjected to silica gel chromatography by using chloroform:methanol=100:1 as an eluent to obtain the title compound (710 mg).

$^1$H-NMR (CDCl$_3$, δ): 1.6–2.1 (4H, m), 3.51 (2H, m), 3.74 (3H, s), 3.94 (3H, s), 4.43 (1H, m), 5.11 (2H, s), 5.53 (1H, m), 6.63 (1H, bs), 7.34 (5H, s), 7.83 (2H, d, J=8.8 Hz), 8.08 (2H, d, J=8.8 Hz).

Reference Example 17

Synthesis of N$^\delta$-(4-methoxycarbonylbenzoyl)-ornithine methyl ester

After adding a 10% palladium-carbon (100 mg) to a methanol solution (100 ml) of the compound (710 mg) of Reference example 16, the mixture was stirred under hydrogen atmosphere at room temperature for 20 hours. Palladium-carbon was removed by filtration using Celite and the solvent was removed under reduced pressure. The residue obtained was subjected to silica gel chromatography by using chloroform:methanol=100:3 as an eluent to obtain the title compound (410 mg).

¹H-NMR (CDCl₃, δ): 1.6–2.1 (4H, m), 3.49 (3H, m), 3.73 (3H, s), 3.94 (3H, s), 7.20 (1H, m), 7.84 (2H, d, J=8.3 Hz), 8.09 (2H, d, J=8.3 Hz).

Reference Example 18

Synthesis of
Nα-(1-carbobenzoxyindolin-5-carbonyl)-Nδ-(4-methoxycarbonylbenzoyl)-ornithine methyl ester By adding thionyl chloride (2.5 ml) to 1-carbobenzoxyindolin-5-carboxylic acid (260 mg) to prepare suspension, and a catalytic amount of dimethylformamide was further added to the suspension and the mixture was stirred at room temperature for 2 hours. Then, the mixture was evaporated to dryness under reduced pressure. The resulting solid material was dissolved in dichloromethane (6 ml), and to the solution were added the compound (245 mg) of Reference example 17 and potassium carbonate (812 mg). Then, water (6 ml) was further added thereto, and the mixture was vigorously stirred at room temperature for 12 hours. Next, the reaction mixture was poured into water and extracted with chloroform, and the chloroform layer was washed with 1N-hydrochloric acid and dried over sodium sulfate. The solvent was removed under reduced pressure. The residue obtained was subjected to silica gel chromatography using chloroform:methanol=100:3 as an eluent to obtain the title compound (310 mg).

¹H-NMR (CDCl₃, δ): 1.7–2.2 (4H, m), 3.16 (2H, t, J=8.3 Hz), 3.61 (1H, m), 3.79 (3H, s), 3.94 (3H, s), 4.11 (2H, t, J=8.3 Hz), 4.83 (1H, m), 5.29 (2H, s), 6.89 (1H, d, J=7.3 Hz), 7.02 (1H, m), 7.40 (5H, m), 7.66 (2H, d, J=7.3 Hz), 7.90 (2H, d, J=8.8 Hz), 8.08 (2H, d, J=8.8 Hz).

Reference Example 19

Synthesis of
Nα-(indolin-5-carbonyl)-Nδ-(4-methoxycarbonylbenzoyl)-ornithine methyl ester To a 30% hydrogen bromide-acetic acid (10 ml) solution of phenol (1.0 g) was added the compound (400 mg) of Reference example 18 and the mixture was stirred at room temperature for 4 hours. Then, when a large amount of ether was added to the reaction mixture, a red-brownish oily product was precipitated. Almost all the ether layer was removed and the oily product was suspended in chloroform. The suspension was washed with a saturated aqueous sodium hydrogen carbonate solution and extracted with chloroform. The chloroform layer was dried over sodium sulfate and the solvent was removed under reduced pressure. White solid obtained was recrystallized from n-hexane-chloroform-methanol to obtain the title compound (145 mg).

¹H-NMR (CDCl₃, δ): 1.6–2.1 (4H, m), 3.05 (2H, t, J=8.3 Hz), 3.48 (2H, m), 3.62 (2H, t, J=8.3 Hz), 3.76 (3H, s), 3.94 (3H, s), 4.75 (1H, m), 6.57 (1H, d, J=7.8 Hz), 7.19 (1H, d, J=7.8 Hz), 7.55 (2H, m), 7.89 (2H, d, J=8.3 Hz), 8.07 (2H, d, J=8.3 Hz).

Example 11

Synthesis of
Nα-[1-[(2,4-diamino-6-pteridinyl)methyl]-indolin-5-carbonyl)-Nδ-(4-methoxycarbonylbenzoyl)-ornithine methyl ester In dimethylacetamide (2.0 ml) were suspended the compound (140 mg) of Reference example 19 and 6-bromomethyl-2,4-diaminopteridine hydrobromide (105 mg) and the suspension was stirred at 50° to 55° C. for 4 hours. After cooling, to the mixture was added water (4 ml) containing triethylamine (32 mg), and the mixture was stirred and then extracted with chloroform. The chloroform layer was dried over sodium sulfate and the solvent was removed under reduced pressure. The residue obtained was subjected to silica gel chromatography by using a mixed solvent of chloroform:methanol=10:1 as an eluent to obtain the title compound (180 mg).

¹H-NMR (CDCl₃, δ): 1.6–2.1 (4H, m), 3.08 (2H, t, J=8.8 Hz), 3.4–3.7 (4H, m), 3.79 (3H, s), 3.94 (3H, s), 4.54 (2H, s), 4.83 (1H, m), 6.52 (1H, d, J=8.3 Hz), 6.79 (1H, d, J=6.8 Hz), 7.17 (1H, m), 7.59 (2H, m), 7.92 (2H, d, J=8.3 Hz), 8.09 (2H, d, J=8.3 Hz), 8.81 (1H, s).

Example 12

Synthesis of
Nα-[1-[(2,4-diamino-6-pteridinyl)methyl]-indolin-5-carbonyl)-Nδ-teleisophthaloyl-ornithine The compound (150 mg) of Example 11 was dissolved in ethanol (24 ml), and 1N-sodium hydroxide aqueous solution (0.8 ml) was further added to the solution and the mixture was stirred at 35° C. for 4.5 hours. After the mixture was stirred at 25° C. for 20 hours, water (1 ml) was added to the reaction mixture and the reaction mixture was evaporated to dryness under reduced pressure. During this procedure, outer temperature was so controlled not to exceeding 30° C. Yellowish solid material obtained was dissolved in water (5 ml), and the solution was adjusted to pH=3.7 with 1N-hydrochloric acid and allowed to stand in a refrigerator for 2 hours. Deposited precipitates were collected by filtration to obtain the title compound (109 mg).

¹H-NMR (CDCl₃, δ): 1.5–2.0 (4H, m), 3.00 (2H, t, J=8.8 Hz), 3.30 (2H, m), 3.58 (2H, t, J=8.8 Hz), 4.36 (1H, m), 4.54 (2H, s), 6.68 (1H, d, J=8.8 Hz), 7.62 (2H, m), 7.91 (2H, d, J=8.3 Hz), 7.99 (2H, d, J=8.3 Hz), 8.10 (1H, d, J=7.8 Hz), 8.61 (1H, m), 8.71 (1H, s). mp; 215°–220° C. (decomposed).

Reference Example 20

Synthesis of α-benzyl
N-t-butoxycarbonyl-γ-anilido-L-glutamate

To a tetrahydrofuran (8 ml) solution of α-benzyl N-t-butoxycarbonyl-L-glutamate (2.2 g) and triethylamine (0.92 ml) was added a tetrahydrofuran (2 ml) solution of isobutyl chlorocarbonate (0.8 ml) at −20° C. under nitrogen atmosphere and the mixture was stirred for 30 minutes. Then, aniline (0.5 ml) was added to the mixture, and the mixture was stirred for one hour. The mixture was returned slowly to room temperature and stirred for further 20 hours. The solvent was removed under reduced pressure and the residue obtained was dissolved in chloroform. The chloroform layer was washed with a saturated sodium hydrogen carbonate aqueous solution, dried over sodium sulfate and then condensed under reduced pressure. The residue obtained was applied to silica gel chromatography by using chloroform:methanol=99:1 as an eluent to obtain the title compound (1.7 g).

¹H-NMR (CDCl₃, δ): 1.44 (9H, s), 1.79–1.97 (1H, m), 2.27–2.40 (2H, m), 4.32–4.44 (1H, m), 5.16 (2H, s), 5.22–5.38 (1H, m), 7.08 (1H, t, J=7.3 Hz), 7.26–7.33 (7H, m), 7.55 (2H, d, J=7.8 Hz), 8.42 (1H, s).

Reference Example 21

Synthesis of α-benzyl γ-anilido-L-glutamate

The compound (1.7 g) of Reference example 20 was dissolved in trifluoroacetic acid (8 ml) under ice cooling and the mixture was stirred for 30 minutes. The solvent was removed under reduced pressure and the residue was dissolved in chloroform. The chloroform layer was washed with a saturated sodium hydrogen carbonate aqueous solution and then dried over sodium sulfate. The solvent was removed under reduced pressure to obtain the title compound (1.3 g).

$^1$H-NMR (CDCl$_3$, δ): 1.86–2.00 (1H, m), 2.17–2.38 (1H, m), 2.42–2.53 (2H, m), 3.53–3.60 (1H, m), 5.15 (2H, s), 7.07 (1H, t, J=7.3 Hz), 7.29–7.35 (7H, m), 7.48 (2H, d, J=7.8 Hz), 8.27 (1H, bs).

Reference Example 22

Synthesis of α-benzyl N-(1-carbobenzoxyindolin-5-carbonyl)-γ-anilido-L-glutamate Thionyl chloride (2 ml) was added to 1-carbobenzoxyindolin-5-carboxylic acid (419 mg) and the mixture was stirred at room temperature for 2 hours. Then, the mixture was evaporated to dryness under reduced pressure. Solid product obtained was dissolved in dichloromethane (2 ml) and to the solution was added dichloromethane (2 ml) solution containing the compound (400 mg) of Reference example 21 and triethylamine (0.21 ml) under ice cooling and nitrogen atmosphere, and the mixture was stirred overnight. The reaction mixture was washed successively with 1N-hydrochloric acid, a saturated sodium hydrogen carbonate aqueous solution and water, dried over sodium sulfate, and then the solvent was removed under reduced pressure. The residue obtained was subjected to silica gel chromatography using, as eluents, dichloromethane and then chloroform to obtain the title compound (317 mg).

$^1$H-NMR (CDCl$_3$, δ): 2.20–2.20 (1H, m), 2.29–2.51 (3H, m), 3.05 (2H, t, J=8.8 Hz), 4.06 (2H, t, J=8.8 Hz), 4.76–4.88 (1H, m), 5.18 (2H, s), 5.28 (2H, bs), 7.05 (1H, t, J=7.3 Hz), 7.18 (1H, d, J=7.8 Hz), 7.23–7.30 (2H, m), 7.33 (5H, s), 7.39 (5H, s), 7.43–7.66 (4H, m), 7.80–7.84 (4H, m), 8.57 (1H, bs).

Reference Example 23

Synthesis of N-(1-carbobenzoxyindolin-5-carbonyl)-γ-anilido-L-glutamic acid

The compound (580 mg) of Reference example 22 was dissolved in a mixed solvent (30 ml) of chloroform:methanol=1:2, and 1N-sodium hydroxide aqueous solution (0.98 ml) was added thereto and the mixture was stirred at room temperature overnight. While maintaining the water bath temperature to 30° C. or lower, the solvent was removed under reduced pressure. The residue obtained was dissolved in water and after the solution was made acidic with 1N-hydrochloric acid, the mixture was extracted by using chloroform. After the chloroform layer was dried over sodium sulfate, the solvent was removed under reduced pressure to obtain the title compound (413 mg ).

$^1$H-NMR (CDCl$_3$, δ): 2.17–2.29 (2H, m), 2.52–2.56 (2H, m), 2.79 (2H, t, J=7.8 Hz), 3.81 (2H, t, J=7.8 Hz), 4.51–4.61 (1H, m), 5.17 (2H, s), 6.94 (1H, t, J=7.3 Hz), 7.13 (2H, t, J=7.8 Hz), 7.34 (5H, s), 7.43–7.65 (5H, m), 8.03 (1H, bs), 9.02 (1H, s).

Reference Example 24

Synthesis of α-methyl N-(1-carbobenzoxyindolin-5carbonyl)-γ-anilido-L-glutamate

The compound (470 mg) of Reference example 23 was dissolved in dried methanol (20 ml), and trimethylsilyldiazomethane (2 ml) was added to the solution and the mixture was stirred for 10 hours. Trimethylsilyldiazomethane (3 ml) was further added to the mixture and the mixture was stirred for 20 hours. After removing the solvent under reduced pressure, the residue obtained was subjected to silica gel chromatography by using, as eluents, chloroform and then chloroform:methanol=199:1 to obtain the title compound (252 mg).

$^1$H-NMR (CDCl$_3$, δ): 2.06–2.21 (1H, m), 2.31–2.56 (3H, m), 3.08 (2H, t, J=8.8 Hz), 3.77 (3H, s), 4.08 (2H, t, J=8.8 Hz), 4.77–4.87 (1H, m), 5.28 (2H, s), 7.07 (1H, t, J=7.3 Hz), 7.15 (1H, d, J=7.8 Hz), 7.28 (2H, t, J=7.8 Hz), 7.37–7.43 (5H, m), 7.58 (2H, d, J=7.8 Hz), 7.62–7.68 (2H, m), 7.86 (1H, bs), 8.67 (1H, bs).

Reference Example 25

Synthesis of α-methyl N-(indolin-5-carbonyl)-γ-anilido-L-glutamate

After adding 10% palladium-carbon (50 mg) to a methanol solution (10 ml) of the compound (250 mg) of Reference example 24, the mixture was stirred under a hydrogen atmosphere at room temperature for 15 hours. Palladium-carbon was removed by filtration using Celite, and the solvent was removed under reduced pressure. The residue obtained was subjected to silica gel chromatography using, as eluents, chloroform:methanol=99:1 and then chloroform:methanol=19:1 to obtain the title compound (172 mg).

$^1$H-NMR (CDCl$_3$, δ): 1.99–2.13 (1H, m), 2.36–2.55 (3H, m), 3.03 (2H, t, J=8.8 Hz), 3.64 (2H, t, J=8.8 Hz), 3.77 (3H, s), 4.08 (1H, bs), 4.79–4.88 (1H, m), 6.55 (1H, d, J=8.3 Hz), 6.92 (1H, d, J=7.3 Hz), 7.08 (1H, t, J=7.3 Hz), 7.30 (2H, t, J=7.8 Hz), 7.53–7.65 (4H, m), 9.01 (1H, bs).

Example 13

Synthesis of α-methyl N-[1-[(2,4-diamino-6-pteridinyl)methyl]-indolin-5-carbonyl]-γ-anilido-L-glutamate In dimethylacetamide (5 ml) were suspended the compound (169 mg) of Reference example 25 and 6-bromomethyl-2,4-diaminopteridine hydrobromide isopropanol adduct (223 mg), and the suspension was stirred at room temperature for 24 hours. The reaction mixture was applied to silica gel chromatography by using, as eluents, ethyl acetate and then chloroform:methanol=19:1 to obtain the title compound (82 mg).

$^1$H-NMR (CDCl$_3$, δ): 2.01–2.09 (1H, m), 2.39–2.48 (3H, m), 3.04 (2H, t, J=8.8 Hz), 3.58 (2H, t, J=8.8 Hz), 3.78 (3H, s), 4.53 (2H, s), 4.79–4.89 (1H, m), 6.48 (1H, d, J=7.8 Hz), 6.87 (1H, d, J=7.3 Hz), 7.08 (1H, t, J=7.8 Hz), 7.26–7.32 (2H, m), 7.59–7.64 (4H, m), 8.81 (1H, s).

Example 14

Synthesis of N-[1-[(2,4-diamino-6-pteridinyl)methyl]-indolin-5-carbonyl]-γ-anilido-L-glutamic acid The compound (82 mg) of Example 13 was dissolved in a mixed solvent (15 ml) of ethanol:water=2:1, and 1N-sodium hydroxide aqueous solution (0.15 ml) was further added to the solution and the mixture was stirred at room temperature for 60 hours. While maintaining the temperature of the water bath 30° C. or lower, the solvent was removed under reduced pressure. The residue obtained was dissolved in a saturated aqueous sodium hydrogen carbonate solution and the solution was adjusted to pH=3.7 with 1N-hydrochloric acid. Deposited orange precipitates were collected by filtration to obtain the title compound (61 mg).

$^1$H-NMR (DMSO-d$_6$, δ): 1.99–2.23 (2H, m), 2.42–2.51 (2H, m), 2.98 (2H, t, J=7.8 Hz), 3.59 (2H, t, J=8.3 Hz), 4.32–4.43 (1H, m), 4.56 (2H, s), 6.70 (1H, t, J=7.8 Hz), 6.90 (2H, bs), 7.00 (1H, d, J=7.8 Hz), 7.26 (2H, t, J=7.8 Hz), 7.55–7.66 (4H, m), 7.72–7.85 (1H, m), 7.89–7.97 (1H, m), 8.20 (1H, d, J=7.3 Hz), 8.75 (1H, s), 9.93 (1H, s).

Reference Example 26

Synthesis of α-benzyl N-t-butoxycarbonyl-γ-(2-methoxycarbonylanilido)-L-glutamate N,N'-carbonyldiimidazole (262 mg) was added to a tetrahydrofuran solution (5 ml) of α-benzyl N-t-butoxycarbonyl-L-glutamate under ice cooling and nitrogen atmosphere, and the mixture was stirred for one hour. Then, a tetrahydrofuran solution (2 ml) of methyl o-aminobenzoate (0.19 ml) was added thereto, and the mixture was stirred for 5 hours. After gradually returning the temperature to room temperature, the mixture was stirred for a further 48 hours. The solvent was removed under reduced pressure, and the residue obtained was applied to silica gel chromatography using chloroform as an eluent to obtain the title compound (273 mg).

$^1$H-NMR (CDCl$_3$, δ): 1.41 (9H, s), 2.04–2.18 (1H, m), 2.20–2.32 (1H, m), 2.48–2.57 (2H, m), 3.92 (3H, s), 4.34–4.47 (1H, m), 5.18 (2H, s), 5.19–5.27 (1H, m), 7.08 (1H, t, J=7.8 Hz), 7.34 (5H, s), 7.53 (1H, t, J=7.3 Hz), 8.02 (1H, d, J=7.8 Hz), 8.68 (1H, d, J=7.8 Hz), 11.06 (1H, s).

Reference Example 27

Synthesis of α-benzyl γ-(2-methoxycarbonylanilido)-L-glutamate

The compound (632 mg) of Reference example 26 was dissolved in trifluoroacetic acid (4.5 ml) under ice cooling and the mixture was stirred for 90 minutes. The solvent was removed under reduced pressure, and the residue was dissolved in chloroform. The chloroform layer was washed with a saturated aqueous sodium hydrogen carbonate solution and dried over sodium sulfate, and the solvent was removed under reduced pressure. The residue obtained was subjected to silica gel chromatography by using, as eluents, chloroform and then chloroform:methanol=97:3 to obtain the title compound (413 mg).

$^1$H-NMR (CDCl$_3$, δ): 1.91–2.02 (1H, m), 2.20–2.30 (1H, m), 2.55–2.64 (2H, m), 3.56–3.62 (1H, m), 3.92 (3H, s), 5.17 (2H, s), 7.07 (1H, t, J=8.3 Hz), 7.35 (5H, s), 7.53 (1H, t, J=8.8 Hz), 8.02 (1H, d, J=8.3 Hz), 8.69 (1H, d, J=8.8 Hz), 11.08 (1H, bs).

Reference Example 28

Synthesis of 1-[(2,4-diamino-6-pteridinyl)methyl]-indolin-5-carboxylic acid

In dimethylacetamide (2 ml) were suspended 1-carbobenzoxyindolin-5-carboxylic acid (87 mg) and 6-bromomethyl-2,4-diaminopteridine hydrobromide 1/2 isopropanol adduct (136 mg), and the suspension was stirred at 55° C. for 4 hours. To the reaction mixture was added water (20 ml) and the mixture was allowed to stand in a refrigerator overnight. Precipitated solid was collected by filtration, dissolved in a small amount of 1N-sodium hydroxide aqueous solution and the solution was adjusted to pH=6.5 with 1N-hydrochloric acid. Deposited brownish precipitates were collected by filtration to obtain the title compound (56 mg).

$^1$H-NMR (DMSO-d$_6$, δ): 3.01 (2H, t, J=8.8 Hz), 3.64 (1H, t, J=8.8 Hz), 4.60 (2H, s), 6.68 (1H, d, J=8.3 Hz), 7.16 (2H, bs), 7.58 (1H, s), 7.65 (1H, d, J=8.3 Hz), 8.09 (1H, bs), 8.25 (1H, bs), 8.77 (1H, s).

Example 15

Synthesis of α-benzyl N-[1-[(2,4-diamino-6-pteridinyl)methyl]-indolin-5-carbonyl]-γ-(2-methoxycarbonylanilido)-L-glutamate To a dimethylformamide suspension (5 ml) of the compound (134 mg) of Reference Example 28 and 1-hydroxybenzotriazole (108 mg) was added a dimethylformamide solution (1.5 ml) of dicyclohexylcarbodiimide (123 mg) under ice cooling and nitrogen atmosphere, and the mixture was stirred for 30 minutes. Then, a dimethylformamide solution (1.5 ml) of the compound of Reference example 27 was added to the mixture, the mixture was gradually returned to room temperature and stirred for 24 hours. The reaction mixture was subjected to silica gel chromatography by using, as eluents, ethyl acetate and then chloroform:methanol=19:1 to obtain the title compound (29 mg).

$^1$H-NMR (CDCl$_3$, δ): 2.32–2.46 (2H, m), 2.46–2.70 (2H, m), 2.96 (2H, t, J=8.8 Hz), 3.49 (2H, t, J=8.3 Hz), 3.89 (3H, s), 4.46 (2H, s), 4.83–4.90 (1H, m), 5.20 (2H, s), 6.40 (1H, d, J=8.3 Hz), 7.05 (1H, t, J=8.3 Hz), 7.14 (1H, d, J=7.8 Hz), 7.34 (5H, s), 7.41–7.59 (3H, m), 7.96 (1H, d, J=8.3 Hz), 8.64 (1H, d, J=8.3 Hz), 8.77 (1H, s).

Example 16

Synthesis of N-[1-[(2,4-diamino-6-pteridinyl)methyl]-indolin-5-carbonyl]-γ-(2-methoxycarbonylanilido)-L-glutamic acid The compound (28 mg) of Example 15 was suspended in methanol (2.5 ml), and 1N-sodium hydroxide aqueous solution (0.41 ml) was added to the suspension and the mixture was stirred at 10° C. for 5 hours. While maintaining the temperature of water bath to 30° C. or lower, the solvent was removed under reduced pressure. The residue obtained was dissolved in a saturated aqueous sodium hydrogen carbonate solution and the solution was adjusted to pH=3.7 with 1N-hydrochloric acid. Deposited orange precipitates were collected by filtration to obtain the title compound (21 mg).

$^1$H-NMR (DMSO-d$_6$, δ): 1.95–2.25 (2H, m), 2.39–2.58 (2H, m), 2.98 (2H, t, J=8.3 Hz), 3.59 (2H, t, J=8.3 Hz), 4.38–4.50 (1H, m), 4.57 (2H, s), 6.69 (1H, d, J=8.3 Hz), 7.12 (1H, t, J=7.8 Hz), 7.24–7.35 (2H, m), 7.51–7.64 (3H, m), 7.96 (1H, d, J=7.8 Hz), 8.04–8.39 (4H, m), 8.47 (1H, d, J=7.8 Hz), 8.78 (1H, s), 11.25 (2H, s).

Reference Example 29

Synthesis of α-methyl γ-benzyl N-t-butoxycarbonyl-L-glutamate

In a dimethylformamide (75 ml) solution of γ-benzyl N-t-butoxycarbonyl-L-glutamate was suspended sodium hydrogen carbonate (2.5 g), and then a dimethylformamide (75 ml) solution of methyl iodide (10.52 g) was added to the suspension and the mixture was stirred at room temperature for 24 hours. After the reaction mixture was condensed under reduced pressure, water (70 ml) was added to the residue and the mixture was extracted with ethyl acetate:n-hexane=1:1 solution. The organic layer was washed with water and dried over sodium sulfate, and the solvent was removed under reduced pressure. The residue obtained was subjected to silica gel chromatography by using ethyl acetate:n-hexane=1:2 as an eluent to obtain the title compound (5.2 g).

$^1$H-NMR (CDCl$_3$, δ): 1.43 (9H, s), 1.92–2.01 (1H, m), 2.11–2.37 (1H, m), 2.42–2.51 (2H, m), 3.73 (3H, s), 4.23–4.40 (1H, m), 5.12 (2H, s), 7.35 (5H, s).

Reference Example 30

Synthesis of α-methyl N-t-butoxycarbonyl-L-glutamate

After adding 10% palladium-carbon (1.1 g) to a methanol solution (30 ml) of the compound (5.2 g) of Reference example 29, the mixture was stirred under hydrogen atmosphere at room temperature for 15 hours. Palladium-carbon was removed by filtration using Celite and the solvent was removed under reduced pressure. The residue obtained was dissolved in a saturated aqueous sodium hydrogen carbonate solution and the solution was washed with chloroform. After separating the aqueous layer, the aqueous layer was adjusted to pH=4 with 5% citric acid and then extracted with chloroform. The chloroform layer was dried over sodium sulfate and the solvent was removed under reduced pressure to obtain the title compound (3.9 g).

$^1$H-NMR (CDCl$_3$, δ): 1.44 (9H, s), 1.89–2.04 (1H, m), 2.09–2.27 (1H, m), 3.75 (3H, s), 4.34 (1H, m), 5.17–5.21 (1H, m), 9.38 (1H, bs).

Reference Example 31

Synthesis of α-methyl N-t-butoxycarbonyl-γ-(3-ethoxycarbonylanilido)-L-glutamate To a dichloromethane suspension (10 ml) of the compound (1.6 g) of Reference example 30 and 1-hydroxybenzotriazole (0.8 g) was added a dichloromethane solution (5 ml) of dicyclohexylcarbodiimide (1.5 g) under ice cooling and nitrogen atmosphere, and the mixture was stirred for 30 minutes. Then, ethyl m-aminobenzoate (1.5 g) was added thereto, the mixture was gradually returned to room temperature and stirred for 20 hours. The solvent was removed under reduced pressure and to the residue obtained was added ethyl acetate, and white insolubles were filtered off. The filtrate was condensed under reduced pressure and the residue obtained was subjected to silica gel chromatography by using, as eluents, chloroform and then chloroform:methanol=99:1 to obtain the title compound (2.5 g).

$^1$H-NMR (CDCl$_3$, δ): 1.38 (3H, t, J=7.1 Hz), 1.47 (9H, s), 1.82–2.04 (1H, m), 2.20–2.39 (1H, m), 2.45–2.51 (2H, m), 3.74 (3H, s), 4.32–4.43 (1H, m), 4.37 (2H, q, J=7.1 Hz), 5.37 (1H, bd, J=7.3 Hz), 7.40 (1H, t, J=7.8 Hz), 7.78 (1H, d, J=7.8 Hz), 7.96 (1H, d, J=9.3 Hz), 8.13 (1H, s), 8.83 (1H, bs).

Reference Example 32

Synthesis of α-methyl γ-(3,ethoxycarbonylanilido)-L-glutamate

The compound (2.5 g) of Reference example 31 was dissolved in trifluoroacetic acid (15 ml) under ice cooling and the solution was stirred for one hour. The solvent was removed under reduced pressure and the residue was dissolved in chloroform. The chloroform layer was washed with a saturated aqueous sodium hydrogen carbonate solution and dried over sodium sulfate, and the solvent was removed under reduced pressure. The residue obtained was subjected to silica gel chromatography by using chloroform:methanol=19:1 as an eluent to obtain the title compound (1.6 g).

$^1$H-NMR (CDCl$_3$, δ): 1.39 (3H, t, J=7.1 Hz), 1.74 (2H, s), 1.82–1.99 (1H, m), 2.15–2.32 (1H, m), 2.52–2.62 (2H, m), 3.54–3.60 (1H, m), 3.74 (3H, s), 4.37 (2H, q, J=7.1 Hz), 7.39 (1H, t, J=7.8 Hz), 7.77 (1H, d, J=7.3 Hz), 7.94 (1H, d, J=7.8 Hz), 7.99 (1H, s), 8.63 (1H, bs).

Reference Example 33

Synthesis of α-methyl N-(1-carbobenzoxyindolin-5-carbonyl)-γ-(3-ethoxycarbonylanilido)-L-glutamate Thionyl chloride (4 ml) was added to 1-carbobenzoxyindolin-5-carboxylic acid (612 mg), and the mixture was stirred at room temperature for 2 hours. Then, the mixture was evaporated to dryness under reduced pressure. Solid material obtained was dissolved in dichloromethane (4 ml) and to the solution was added a dichloromethane solution (4 ml) containing the compound (529 mg) of Reference example 32 and triethylamine (0.36 ml) under ice cooling and nitrogen atmosphere, and the mixture was stirred overnight. The reaction mixture was successively washed with 2N-hydrochloric acid, a saturated aqueous sodium hydrogen carbonate solution and water, and dried over sodium sulfate, and then the solvent was removed under reduced pressure. The residue obtained was applied to silica gel chromatography by using, as eluents, chloroform and then chloroform:methanol=99:1 to obtain the title compound (870 mg).

$^1$H-NMR (CDCl$_3$, δ): 1.37 (3H, t, J=7.1 Hz), 2.08–2.22 (1H, m), 2.36–2.57 (3H, m), 3.06 (2H, t, J=8.8 Hz), 3.77 (3H, s), 4.07 (2H, t, J=8.8 Hz), 4.30–4.40 (2H, q, J=7.1 Hz), 4.78–4.87 (1H, m), 5.28 (2H, bs), 7.13 (1H, d, J=7.8 Hz), 7.30–7.43 (6H, m), 7.60–7.67 (2H, m), 7.74 (1H, d, J=7.8 Hz), 7.89 (1H, d, J=7.8 Hz), 8.12 (1H, bs), 8.96 (1H, bs).

Reference Example 34

Synthesis of α-methyl N-(indolin-5-carbonyl)-γ-(3-ethoxycarbonylanilido)-L-glutamate After adding 10% palladium-carbon (0.17 g) to a methanol solution (11 ml) of the compound (842 mg) of Reference example 33, the mixture was stirred under hydrogen atmosphere at room temperature for 15 hours. Palladium-carbon was removed by filtration using Celite, and the solvent was removed under reduced pressure. The residue obtained was subjected to silica gel chromatography using, as eluents, chloroform and then chloroform:methanol=99:1 to obtain the title compound (448 mg).

$^1$H-NMR (CDCl$_3$, δ): 1.36 (3H, t, J=7.1 Hz), 2.05–2.25 (1H, m), 2.25–2.48 (1H, m), 2.48–2.59 (2H, m), 2.93 (2H, t, J=8.8 Hz), 3.57 (2H, t, J=8.8 Hz), 3.71 (3H, s), 4.18 (1H, bs), 4.34 (2H, t, q, J=7.1 Hz), 4.73–4.84 (1H, m), 6.46 (1H, d, J=8.8 Hz), 7.16 (1H, d, J=7.8 Hz), 7.32 (1H, t, J=7.8 Hz), 7.50–7.53 (2H, m), 7.73 (1H, d, J=7.8 Hz), 7.87 (1H, d, J=7.3 Hz), 8.19 (1H, s), 9.39 (1H, bs).

Example 17

Synthesis of α-methyl N-[1-[(2,4-diamino-6-pteridinyl)methyl]-indolin-5-carbonyl]-γ-(3-ethoxycarbonylanilido)-L-glutamate To dimethylacetamide (5 ml) were suspended the compound (448 mg) of Reference Example 34 and 6-bromo-2,4-diaminopteridine hydrobromide isopropanol adduct (587 mg) and the suspension was stirred at room temperature for 36 hours. The reaction mixture was applied to silica gel chromatography by using, as eluents, ethyl acetate and then chloroform:methanol=9:1 to obtain the title compound (653 mg).

$^1$H-NMR (DMSO-d$_6$, δ): 1.34 (3H, t, J=6.8 Hz), 1.96–2.32 (2H, m), 2.32–2.59 (2H, m), 3.00 (2H, t, J=7.3 Hz), 3.56–3.66 (5H, s), 4.32 (2H, q, J=6.5 Hz), 4.40–4.56 (3H, m), 6.66–6.71 (3H, bs), 7.39 (1H, t, J=7.8 Hz), 7.63–7.67 (3H, m), 7.84 (1H, d, J=7.3 Hz), 8.22 (1H, s), 8.32 (1H, d, J=7.3 Hz), 8.73 (1H, s), 10.11 (1H, s).

Example 18

Synthesis of N-[1-[(2,4-diamino-6-pteridinyl)methyl]-indolin-5-carbonyl]-γ-(3-carboxyanilido)-L-glutamic acid The compound (303 mg) of Example 17 was dissolved in methanol (10 ml), and 1N-sodium hydroxide aqueous solution (1.06 ml) was added to the solution and the mixture was stirred at room temperature for 12 hours. Water (1 ml) was added and then the mixture was further stirred for 2 hours. While maintaining the temperature of water bath to 30° C. or lower, the solvent was removed under reduced pressure. The residue obtained was dissolved in a saturated aqueous sodium hydrogen carbonate solution and the solution was adjusted to pH=3.7 with 1N-hydrochloric acid. Deposited orange precipitates were collected by filtration to obtain the title compound (157 mg).

$^1$H-NMR (DMSO-d$_6$, δ): 1.97–2.25 (2H, m), 2.42–2.58 (2H, m), 2.99 (2H, t, J=8.8 Hz), 3.59 (2H, t, J=8.8 Hz), 4.33–4.45 (1H, m), 4.59 (2H, s), 6.71 (1H, d, J=8.3 Hz), 6.93 (2H, bs), 7.39 (1H, t, J=7.8 Hz), 7.57–7.82 (5H, m), 7.88–8.04 (1H, m), 8.06–8.12 (1H, m), 8.15–8.26 (2H, m), 8.75 (1H, s), 10.12 (1H, s).

Reference Example 35

Synthesis of α-benzyl N-carbobenzoxy-N',N'-dimethyl-L-glutamate

Ethyl chlorocarbonate (0.14 ml) was added to a tetrahydrofuran solution (2 ml) containing α-benzyl N-carbobenzoxy-L-glutamate (508 mg) and triethylamine (0.19 ml) at −20° C. under nitrogen atmosphere, and the mixture was stirred for 30 minutes. Then, a dichloromethane (3 ml) solution of dimethylamine hydrochloride (112 mg) and triethylamine (0.19 ml) was added to the mixture and the mixture was stirred for one hour. The mixture was gradually returned to room temperature, and the residue obtained was dissolved in chloroform. The chloroform layer was washed successively with a saturated aqueous sodium hydrogen carbonate solution and 1N-hydrochloric acid, and dried over sodium sulfate, and then the solvent was removed under reduced pressure. The residue obtained was subjected to silica gel chromatography by using chloroform:methanol=49:1 as an eluent to obtain the title compound (453 mg).

$^1$H-NMR (CDCl$_3$, δ): 1.97–2.37 (4H, m), 2.86 (3H, s), 2.90 (3H, s), 4.39–4.41 (1H, m), 5.10 (2H, s), 5.17 (2H, s), 5.86–5.89 (1H, m), 7.34 (10H, s).

Reference Example 36

Synthesis of N-carbobenzoxy-N',N'-dimethyl-L-glutamine

To a methanol solution (5 ml) of the compound (450 mg) of Reference example 35 was added 1N-sodium hydroxide aqueous solution and the mixture was stirred at room temperature overnight. While maintaining the water bath temperature to 30° C. or lower, the solvent was removed under reduced pressure. The residue obtained was dissolved in water and after the solution was made acidic with 1N-hydrochloric acid, the mixture was extracted by using chloroform. After the chloroform layer was dried over sodium sulfate, the solvent was removed under reduced pressure to obtain the title compound (341 mg).

$^1$H-NMR (CDCl$_3$, δ): 1.93–2.06 (1H, m), 2.21–2.33 (1H, m), 2.42–2.56 (1H, m), 2.76–2.84 (1H, m), 2.98 (3H, s), 3.00 (3H, s), 4.19–4.27 (1H, m), 5.09 (2H, s), 6.04–6.06 (1H, m), 7.37 (10H, s).

Reference Example 37

Synthesis of α-methyl N-carbobenzoxy-N',N'-dimethyl-L-glutaminate

In a dried methanol (4 ml) was dissolved the compound (3530 mg) of Reference example 36 and trimethylsilyldiazomethane (5 ml) was added to the solution and the mixture was stirred for 2 hours. The solvent was removed under reduced pressure to obtain the title compound (338 mg).

$^1$H-NMR (CDCl$_3$, δ): 1.96–2.43 (4H, m), 2.92 (3H, s), 2.95 (3H, s), 3.74 (3H, s), 4.28–4.40 (1H, m), 5.10 (2H, s), 5.80 (1H, m), 7.35 (5H, s).

Reference Example 38

Synthesis of α-methyl N',N'-dimethyl-L-glutaminate

After adding a 10% palladium-carbon (70 mg) to a methanol solution (10 ml) of the compound (580 mg) of Reference example 37, the mixture was stirred under hydrogen atmosphere at room temperature for 15 hours. Palladium-carbon was removed by filtration using Celite and the solvent was removed under reduced pressure. The residue obtained was subjected to silica gel chromatography by using chloroform:methanol=19:1 as an eluent to obtain the title compound (160 mg).

$^1$H-NMR (CDCl$_3$, δ): 1.74–1.92 (1H, m), 2.06–2.23 (1H, m), 2.47 (2H, t, J=7.3 Hz), 2.95 (3H, s), 3.02 (3H, s), 3.49–3.56 (1H, m), 3.73 (3H, s).

Reference Example 39

Synthesis of α-methyl
N-(1-carbobenzoxyindolin-5-carbonyl)-N',N'-dimethyl-L-glutaminate Thionyl chloride (2 ml) was added to 1-carbobenzoxyindolin-5-carboxylic acid (295 mg) and the mixture was stirred at room temperature for 2 hours. Then, the mixture was evaporated to dryness under reduced pressure. Solid material obtained was dissolved in dichloromethane (2 ml) and to the solution was added a dichloromethane solution (2.5 ml) containing the compound (160 mg) of Reference example 38 and triethylamine (0.18 ml) under ice cooling and nitrogen atmosphere, and the mixture was stirred overnight. The reaction mixture was successively washed with 1N-hydrochloric acid, a saturated aqueous sodium hydrogen carbonate solution and water, and dried over sodium sulfate and then the solvent was removed under reduced pressure. The residue obtained was applied to silica gel chromatography using, as eluents, chloroform and then chloroform:methanol=99:1 to obtain the title compound (359 mg).

$^1$H-NMR (CDCl$_3$, δ): 2.22–2.32 (2H, m), 2.43–2.55 (2H, m), 2.94 (3H, s), 2.98 (3H, s), 3.15 (2H, t, J=8.8 Hz), 3.76 (3H, s), 4.10 (2H, t, J=8.8 Hz), 4.58–4.68 (1H, m), 5.28 (2H, s), 7.36–7.41 (6H, m), 7.71 (1H, s), 7.90 (1H, d, J=5.9 Hz).

Reference Example 40

Synthesis of α-methyl
N-(indolin-5-carbonyl)-N',N'-dimethyl-L-glutaminate

After adding a 10% palladium-carbon (70 mg) to a methanol solution (5 ml) of the compound (359 mg) of Reference example 39, the mixture was stirred under hydrogen atmosphere at room temperature for 15 hours. Palladium-carbon was removed by filtration using Celite and the solvent was removed under reduced pressure. The residue obtained was subjected to silica gel chromatography by using chloroform:methanol=99:1 as an eluent to obtain the title compound (131 mg).

$^1$H-NMR (CDCl$_3$, δ): 2.19–2.30 (2H, m), 2.44–2.53 (2H, m), 2.93 (3H, s), 2.97 (3H, s), 3.04 (2H, t, J=8.3 Hz), 3.62 (2H, t, J=8.3 Hz), 3.75 (3H, s), 4.14 (1H, bs), 4.60–4.70 (1H, m), 6.56 (1H, d, J=7.8 Hz), 7.51–7.62 (3H, m).

Example 19

Synthesis of α-methyl
N-[1-[(2,4-diamino-6-pteridinyl)methyl]-indolin-5-carbonyl]-N',N'-dimethyl-L-glutaminate In dimethylacetamide (4 ml) were suspended the compound (131 mg) of Reference example 40 and 6-bromomethyl-2,4-diaminopteridine hydrobromide isopropanol adduct (233 mg), and the suspension was stirred at room temperature for 24 hours. The reaction mixture was applied to silica gel chromatography by using, as eluents, ethyl acetate and then chloroform:methanol=9:1 to obtain the title compound (95 mg).

$^1$H-NMR (CDCl$_3$, δ): 1.98–2.17 (2H, m), 2.42 (2H, t, J=6.8 Hz), 2.84 (3H, s), 2.94 (3H, s), 3.00 (2H, t, J=8.3 Hz), 3.59 (2H, t, J=8.3 Hz), 3.64 (3H, s), 4.30–4.42 (1H, m), 4.55 (2H, s), 6.68 (1H, d, J=7.3 Hz), 7.60–7.64 (2H, m), 8.34 (1H, d, J=7.3 Hz), 8.71 (1H, s).

Example 20

Synthesis of
N-[1-[(2,4-diamino-6-pteridinyl)methyl]-indolin-5-carbonyl]-N',N'-dimethyl-L-glutamine The compound (70 mg) of Example 19 was dissolved in methanol (5 ml) and to the solution was added 1N-sodium hydroxide aqueous solution (0.15 ml), and the mixture was stirred at room temperature for 12 hours. Water (2 ml) was added thereto and the mixture was further stirred for 5 hours. While maintaining the water bath temperature to 30° C. or lower, the solvent was removed under reduced pressure. The residue obtained was dissolved in a saturated aqueous sodium hydrogen carbonate solution and the solution was adjusted to pH=3.7 with 1N-hydrochloric acid. Deposited orange precipitates were collected by filtration to obtain the title compound (16 mg).

$^1$H-NMR (DMSO-d$_6$, δ): 1.96–2.08 (2H, m), 2.41 (2H, t, J=7.1 Hz), 2.82 (3H, s), 2.92 (3H, s), 3.01 (2H, t, J=7.8 Hz), 3.62 (2H, t, J=7.8 Hz), 4.27–4.37 (1H, m), 4.62 (2H, s), 6.72 (1H, d, J=8.8 Hz), 7.61–7.64 (2H, m), 8.24 (1H, d, J=6.8 Hz), 8.87 (1H, s), 12.46 (1H, bs).

Reference Example 41

Synthesis of
[1-[(2,4-diamino-6-pteridinyl)methyl]1,2,3,4-tetrahydro-6-quinolinecarboxylic acid In dimethylacetamide (3 ml) were suspended 6-bromomethyl-2,4-diaminopteridine hydrobromide.isopropanol adduct (178 mg) and 1,2,3,4-tetrahydro-6-quinolinecarboxylic acid (55 mg), and the suspension was stirred at 60° to 65° C. overnight. After cooling, water (10 ml) was added to the reaction mixture, and the mixture was adjusted to pH=3.5 with 1N-hydrochloric acid under ice-water cooling and allowed to stand at cool place overnight. Deposited precipitates were collected by filtration to obtain the title compound (70 mg).

$^1$H-NMR (DMSO-d$_6$, δ): 2.08 (2H, t, J=8 Hz), 2.88 (2H, t, J=8 Hz), 3.68 (2H, t, J=8 Hz), 4.72 (2H, s), 6.62 (1H, d, J=9 Hz), 7.48 (2H, m), 8.51 (1H, s).

Example 21

Synthesis of diethyl
N-[1-[(2,4-diamino-6-pteridinyl)methyl]1,2,3,4-tetrahydro-6-quinolinecarbonyl]-L-glutamate In anhydrous dimethylformamide (6 ml) were suspended triethylamine (60 mg) and diethylphosphorcyanidate (98 mg), and the compound (60 mg) of Reference example 41 was further added thereto and the mixture was stirred. After dissolving, the mixture was stirred at 80° C. for 3 minutes, and returned to room temperature, followed by stirring for 10 minutes. Then, triethylamine (20 mg) and diethyl glutamate hydrochloride (40 mg) were added to the mixture and the mixture was stirred at 80° C. for 2 hours. After the reaction, the solvent was removed under reduced pressure, to the residue was added chloroform and the chloroform layer was washed with a saturated aqueous sodium bicarbonate solution. After drying the chloroform layer over magnesium sulfate, the solvent was removed under reduced pressure and the residue obtained was applied to silica gel chromatography by using a mixed solvent of chloroform:methanol=10:1 as an eluent to obtain the title compound (50 mg).

¹H-NMR (DMSO-d₆, δ): 1.1–1.4 (6H, m), 1.8–2.4 (4H, m), 2.40 (2H, t, J=8 Hz), 2.82 (2H, t, J=8 Hz), 3.51 (2H, t, J=8 Hz), 4.0–4.3 (4H, m), 4.64 (1H, m), 4.75 (2H, s), 6.65 (1H, d, J=9 Hz), 7.47 (2H, m), 8.65 (1H, s).

Example 22

Synthesis of N-[1-[(2,4-diamino-6-pteridinyl)methyl]1,2,3,4-tetrahydro-6-quinolinecarbonyl]-L-glutamic acid In ethanol (10 ml) was dissolved the compound (50 mg) of Example 21, and to the solution was added 1N-sodium hydroxide aqueous solution (0.24 ml) at 35° C., and the mixture was stirred at the same temperature for 4.5 hours. Stirring was further continued at 25° C. for 20 hours, and water (1 ml) was added to the reaction mixture. Under ice-water cooling, the reaction mixture was adjusted to pH=3.7 with 1N-hydrochloric acid and allowed to stand at cool place overnight. Deposited precipitates were collected by filtration to obtain the title compound (27 mg).

¹H-NMR (DMSO-d₆, δ): 1.8–2.2 (4H, m), 2.31 (2H, t, J=8 Hz), 2.75 (2H, t, J=8 Hz), 3.60 (2H, t, J=8 Hz), 4.36 (1H, m), 4.70 (2H, s), 6.62 (1H, d, J=9 Hz), 7.51 (2H, m), 8.62 (1H, s). mp; 204°–208° C. (decomposed).

Reference Example 42

Synthesis of methyl 4-[(2,4-diamino-6-pteridinyl)methyl]-3,4-dihydro-2H-1,4-benzoxazin-7-carboxylate In dimethylacetamide (10 ml) were suspended 6-bromomethyl-2,4-diaminopteridine hydrobromide.isopropanol adduct (410 mg) and methyl 3,4-dihydro-2H-1,4-benzoxazin-7-carboxylate (200 mg), and the suspension was stirred at a bath temperature of 65° C. for 4 hours and at 90° C. for 19 hours. After cooling, dimethylacetamide was condensed under reduced pressure, and chloroform and an aqueous sodium hydrogen carbonate solution were added to the condensate. After precipitates were filtered off, the organic layer was washed with water and dried over magnesium sulfate, and the solvent was removed under reduced pressure. The residue was subjected to silica gel chromatography and eluted by using a mixed solvent of chloroform:methanol=97:3 to obtain the title compound (100 mg).

¹H-NMR (CDCl₃:CD₃OD=9:1, δ): 3.63 (2H, brt), 3.84 (3H, s), 4.32 (2H, brt), 4.72 (2H, s), 6.68 (1H, d, J=9.0 Hz), 7.47 (1H, s), 7.50 (1H, d, J=9.0 Hz ), 8.71 (1H, s).

Reference Example 43

Synthesis of 4-[(2,4-diamino-6-pteridinyl)methyl]-3,4-dihydro-2H-1,4-benzoxazin-7-carboxylic acid The compound (60 mg) of Reference example 42 was suspended in a mixed solvent of 1N-sodium hydroxide aqueous solution (20 ml) and methanol (20 ml) and the suspension was refluxed for 2.5 hours under heating. After cooling, the solvent was removed and water was added and the mixture was adjusted to pH=5 (suspended) with 1N-hydrochloric acid. It was allowed to stand at cool place, deposited precipitates were collected by filtration and dried to obtain the title compound (60.8 mg).

¹H-NMR (DMSO-d₆, δ): 3.63 (2H, m), 4.22 (2H, m), 4.71 (2H, s), 7.21 (1H, s), 8.29 (1H, s).

Example 23

Synthesis of diethyl N-[4-[(2,4-diamino-6-pteridinyl)methyl]-3,4-dihydro-2H-1,4-benzoxazin-7-carbonyl]-L-glutamate To a solution of diethylphosphorcyanidate (64 μl), triethylamine (60 μl) and anhydrous dimethylformamide (5 ml) was added the compound (50 mg) of Reference example 43 and the mixture was stirred under nitrogen atmosphere at 80° C. for 5 minutes. After cooling to the room temperature, triethylamine (20 μl) and diethyl glutamate (34 mg) were added to the mixture and the mixture was again heated to 80° C. and stirred for 2.5 hours. After cooling, the reaction mixture was extracted with chloroform, and the chloroform layer was washed successively with a saturated aqueous sodium hydrogen carbonate solution and a saline solution. After drying the chloroform layer over magnesium sulfate, the solvent was removed under reduced pressure. The residue obtained was subjected to silica gel chromatography by using a mixed solvent of chloroform:methanol=19:1 as an eluent to obtain the title compound (10 mg).

¹H-NMR (CDCl₃:CD₃OD=9:1, δ): 1.23 (3H, t, J=6.8 Hz), 1.29 (3H, t, J=6.8 Hz), 3.60 (2H, m), 4.11 (2H, q, J=6.8 Hz), 4.22 (2H, q, J=6.8 Hz), 4.32 (2H, m), 4.71 (2H, s), 6.69 (1H, d, J=10.0 Hz), 7.29 (1H, d, J=10.0 Hz), 7.36 (1H, s), 8.70 (1H, s).

Example 24

Synthesis of N-[4-[(2,4-diamino-6-pteridinyl)methyl]3,4-dihydro-2H-1,4-benzoxazin-7-carbonyl]-L-glutamic acid In ethanol (3 ml) was dissolved the compound (9 mg) of Example 23, and to the solution was added 1N-sodium hydroxide aqueous solution, and the mixture was stirred at room temperature for 4 days. The solvent was removed and the residue was subjected to silica gel column chromatography by using a mixed solvent of chloroform:methanol:aqueous ammonia=5:4:1. Fractions containing the title compound were collected and the solvent was removed therefrom. The reside was dissolved by adding a saturated aqueous sodium hydrogen carbonate solution (200 μl) and the solution was adjusted to pH about 4 (suspended) by dropping 1N-hydrochloric acid and allowed to stand at cool place overnight. Deposited precipitates were collected by filtration to obtain the title compound (2.8 mg).

¹H-NMR (DMSO-d₆, δ): 1.86–1.95 (1H, m), 1.95–2.03 (1H, m), 2.24–2.38 (2H, m), 3.67 (2H, t, J=3.8 Hz), 4.25 (2H, t, J=3.8 Hz), 4.30 (1H, m), 4.70 (2H, s), 6.83 (1H, d, J=8.6 Hz), 7.26 (1H, s), 7.30 (1H, d, J=8.6 Hz), 8.09 (1H, m), 8.70 (1H, s). IR (KBr) ν max 3464, 1642 and 1512 cm⁻¹.

Example 25

Synthesis of methyl N-[1-[(2,4-diamino-6-pteridinyl)methyl]indolin-5-carbonyl]DL-2-amino-4-phosphonobutyrate In anhydrous dimethylformamide (30 ml) were suspended triethylamine (272 mg) and diethyl cyanophosphonic acid (440 mg). Then, to the suspension was added 1-[(2,4-diamino-6-pteridinyl)methyl]indolin-5-carboxylic acid (303 mg) and the mixture was stirred at room temperature overnight (Solution A). On the other hand, in anhydrous methanol (5 ml) was dissolved DL- 2-amino-4-phosphonobutyric acid at 0° C. and then thionyl chloride (1 ml) was gradually added to the solution at the same temperature. After the mixture was returned to room temperature and stirred overnight, the solvent was removed under reduced pressure. The residue obtained was dissolved in anhydrous dimethylformamide (Solution B). Then, Solutions A and B were mixed. To the mixed solution was further added triethylamine (505 mg) and the mixture was stirred at room temperature for 3 days. Then, the solvent was removed under reduced pressure to obtain a residue (700 mg). From the residue obtained, 100 mg thereof was taken and fractionation was carried out by using a high performance liquid chromatography (column: YMC-A323) with an eluent of water:acetonitrile:trifluoroacetic acid=87.5:12.5:1 to obtain the title compound (2 mg).

$^1$H-NMR (D$_2$O, δ): 1.7–2.3 (4H, m), 3.06 (2H, t, J=8 Hz), 3.58 (2H, t, J=8 Hz), 3.84 (3H, s), 4.36 (1H, m), 4.70 (2H, s), 6.63 (1H, d, J=8.6 Hz), 7.60 (2H, m), 8.78 (1H, s).

Reference Example 44

Synthesis of methyl 4-amino-3-hydroxy-benzoate

In methanol (40 ml) was suspended 4-amino-3-hydroxybenzoic acid and to the suspension was passed through a hydrogen chloride gas for 10 minutes, and the mixture was stirred at room temperature for 6 hours. Deposited precipitates were collected by filtration, washed three times with ether and then vacuum dried to obtain the title compound (4.15 g).

$^1$H-NMR (CDCl$_3$: δ): 3.83 (3H, s), 6.68 (1H, d, J=8 Hz), 7.41 (2H, m).

Reference Example 45

Synthesis 4-methoxycarbonyl-2-hydroxy-chloroacetyl-anilide

In dichloromethane (30 ml) were dissolved the compound (1.0 g) of Reference example 44 and triethylamine (4.0 ml) and the solution was made 0° C. To the solution was added dropwise a dichloromethane solution (5 ml) of chloroacetyl chloride (1.0 ml) under nitrogen atmosphere over 8 minutes, and the mixture was stirred at the same temperature for one hour. Then, to the reaction mixture was added a saturated aqueous ammonium chloride solution and deposited precipitates were collected by filtration. Recrystallization was carried out by using chloroform-acetone to obtain the title compound (0.83 g).

$^1$H-NMR (CDCl$_3$: δ): 3.90 (3H, s), 4.25 (2H, s), 7.52 (2H, m), 8.37 (1H, d, J=8 Hz).

Reference Example 46

Synthesis of methyl 3-oxo-3,4-dihydro-2H-1,4,benzoxazin-7-carboxylate

In ethanol (300 ml) was suspended the compound (6.0 g) of Reference example 45, and to the suspension was added potassium acetate (5.0 g) and the mixture was refluxed under nitrogen atmosphere for 90 minutes. After cooling the reaction mixture, precipitates were collected by filtration and vacuum dried to obtain the title compound (5.2 g).

$^1$H-NMR (DMSO-d$_6$: δ): 3.80 (3H, s), 4.63 (2H, s), 6.95 (1H, m), 7.43 (1H, m), 7.56 (1H, m).

Reference Example 47

Synthesis of methyl 3,4-dihydro-2H-1,4-benzoxazin-7carboxylate

Under nitrogen atmosphere, to tetrahydrofuran (30 ml) were added tetrahydrofuran.borane complex (1[M] solution, 10 ml) and the compound (440 mg) of Reference example 46 at 0° C., and the mixture was stirred at room temperature for 15 minutes, and then reflexed for 4 hours. The reaction mixture was cooled to room temperature and 6N-hydrochloric acid (2.7 ml) was added thereto. The reaction mixture was condensed under reduced pressure and poured into water and made alkaline with 2N-sodium hydroxide aqueous solution. Then, the title compound was extracted with ethyl acetate and the organic layer obtained was washed with a saline solution and dried over magnesium sulfate. After removing the solvent under reduced pressure, the residue obtained was subjected to silica gel column chromatography. The residue was developed and eluted with a mixed solvent of hexane:ethyl acetate=3:2 to obtain the title compound (310 mg).

$^1$H-NMR (CDCl$_3$: δ): 3.46 (2H, m), 3.84 (3H, s), 4.22 (2H, t, J=4.4 Hz), 4.30 (1H, m), 6.53 (1H, d, J=9.8 Hz), 7.45 (1H, s), 7.47 (1H, d, J=9.8 Hz).

Reference Example 48

Synthesis of methyl N-carbobenzoxy-3,4-dihydro-2H-1,4benzoxazin-7-carboxylate

In tetrahydrofuran (50 ml) was dissolved the compound (1.4 g) of Reference example 47, and to the solution was added gradually sodium hydride (700 mg) and the mixture was stirred at room temperature for 30 minutes. Then, carbobenzoxy chloride (3 ml) was added to the mixture and the mixture was stirred overnight. After several drops of water were added to the reaction mixture, the reaction mixture was poured into cool water and the title compound was extracted with ethyl acetate. The organic layer obtained was dried over sodium sulfate and the solvent was removed under reduced pressure. The residue was recrystallized from hexan-ethylacetate to obtain the title compound (1.79 g).

$^1$H-NMR (CDCl$_3$: δ): 3.85 (3H, s), 3.91 (2H, m), 4.25 (2H, m), 5.34 (2H, s), 7.35 (5H, m), 7.53 (2H, m), 7.99 (1H, m).

Reference Example 49

Synthesis of N-carbobenzoxy-3,4-dihydro-2H-1,4-benzoxazin-7-carboxylic acid

In ethanol (50 ml) was suspended the compound (1.79 g) of Reference example 48, and to the suspension was added 1N-sodium hydroxide aqueous solution (8.2 ml) and the mixture was stirred overnight. The solvent was removed under reduced pressure and the residue obtained was dissolved in water (20 ml). Then, 1N-hydrochloric acid was gradually added thereto to adjust pH=2, and deposited precipitates were collected by filtration and vacuum dried to obtain the title compound (1.39 g).

$^1$H-NMR (CDCl$_3$: δ): 3.82 (2H, m), 4.14 (2H, m), 5.13 (2H, s), 7.2–7.7 (7H, m), 7.95 (1H, m).

Reference Example 50

Synthesis of dimethyl N-(3,4-dihydro-2H-1,4-benzoxazin-7-carbonyl)-L-α-amino-adipate In thionyl chloride (5 ml) was suspended the compound (800 mg) of Reference example 49, and a catalytic amount of dimethylformamide was added to the mixture and the mixture was stirred at room temperature for 2 hours. Then, excess thionyl chloride was removed under reduced pressure, and the residue was triturated with hexane. After collecting the resulting crystals by filtration, the crystals were dissolved in dichloromethane (20 ml) and to the dichloromethane solution was added dropwise an aqueous solution containing L-α-amino-adipic acid dimethyl ester hydrochloride (1.0 g) and triethylamine (1.0 g) under ice-water cooling. The mixture was stirred at room temperature overnight, and the solvent was removed under reduced pressure. To the residue was added a mixed solution of ethyl acetate and dil. hydrochloric acid under ice-water cooling. After stirring for 5 minutes, the organic layer was separated and then the organic layer was washed with a saturated aqueous sodium hydrogen carbonate solution. After drying over magnesium sulfate, the solvent was removed under reduced pressure. The residue obtained was dissolved in ethanol (80 ml) and after adding 10%-palladium-carbon (400 mg), the mixture was stirred under hydrogen atmosphere at room temperature overnight. Palladium-carbon was removed by filtration using Celite, and the solvent was removed under reduced pressure. The residue obtained was subjected to silica gel column chromatography by using chloroform:methanol = 100:1 as an eluent to obtain the title compound (230 mg).

$^1$H-NMR (CDCl$_3$; δ): 1.6–2.1 (4H, m), 2.38 (2H, t, J=6.8 Hz), 3.46 (2H, m), 3.68 (3H, s), 3.77 (3H, s), 4.24 (2H, m), 4.72 (1H, m), 6.59 (1H, d, J=8.3 Hz), 7.33 (2H, m).

Example 26

Synthesis of dimethyl N-[1-[(2,4-diamino)-6-pteridinyl)methyl]-3,4-dihydro-2H-1,4-benzoxazin-7-carbonyl]-L-αamino-adipate In dimethylacetamide (3 ml) were suspended the compound (200 mg) of Reference example 50 and 6-bromomethyl-2,4-diaminopteridine hydrobromide.isopropanol adduct (226 mg), and the suspension was stirred at 60° C. for 6 hours. After cooling, the reaction mixture was poured into a saturated aqueous sodium hydrogen carbonate solution and extracted with chloroform. The organic layer was dried over magnesium sulfate and the solvent was removed under reduced pressure. The residue obtained was subjected to silica gel column chromatography by using a mixed solvent of chloroform:methanol = 10:1 as an eluent to obtain the title compound (260 mg).

$^1$H-NMR (CD$_3$OD, δ): 1.6–2.0 (4H, m), 2.36 (2H, t, J=6.8 Hz), 3.58 (2H, m), 3.66 (3H, s), 3.76 (3H, s), 4.39 (2H, m), 4.67 (2H, bs), 4.73 (1H, m), 6.66 (1H, d, J=8.3 Hz), 6.99 (1H, t, J=7.3 Hz), 7.29 (2H, m), 8.70 (1H, s).

Example 27

Synthesis of N-[1-[(2,4-diamino)-6-pteridinyl)methyl]-3,4-dihydro-2H-1,4-benzoxazin-7-carbonyl]-L-α-amino-adipic acid The compound (260 mg) of Example 26 was dissolved in ethanol (12 ml), and 1N-sodium hydroxide aqueous solution (0.45 ml) was added to the solution at 35° C. and the mixture was stirred at the same temperature for 4 hours. After continuing stirring at 25° C. for 20 hours, water (0.5 ml) was added to the reaction mixture and ethanol was removed under reduced pressure. The residue obtained was dissolved in water (6 ml), adjusted to pH=3.7 with 1N-hydrochloric acid under ice-water cooling and allowed to stand overnight at cool place. Deposited precipitates were collected by filtration to obtain the title compound (176 mg).

$^1$H-NMR (DMSO-d$_6$, δ): 1.5–2.0 (4H, m), 2.14 (2H, t, J=6.8 Hz), 3.68 (2H, m), 4.28 (3H, m), 4.71 (2H, bs), 6.80 (1H, t, J=8.3 Hz), 7.31 (2H, m), 8.13 (1H, d, J=7.3 Hz), 8.71 (1H, s).

Reference Example 51

Synthesis of α-methyl γ-benzyl N-t-butoxycarbonyl-L-glutamate

In a dimethylformamide solution (75 ml) of γ-benzyl N-t-butoxycarbonyl-L-glutamate (5.0 g) was suspended sodium hydrogen carbonate (2.5 g), and a dimethylformamide solution (75 ml) of methyl iodide (10.5 g) was added to the suspension and the mixture was stirred at room temperature for 24 hours. After the reaction mixture was condensed under reduced pressure, the residue was poured into water (70 ml) and extracted with a mixed solution of ethyl acetate:n-hexane=1:1. The organic layer was washed with water and dried over sodium sulfate, and the solvent was removed under reduced pressure. The residue obtained was subjected to silica gel column chromatography by using ethyl acetate:n-hexane=1:2 as an eluent to obtain the title compound (5.2 g).

$^1$H-NMR (CDCl$_3$, δ): 1.43 (9H, s), 1.92–2.01 (1H, m), 2.11–2.37 (1H, m), 2.42–2.51 (2H, m), 3.73 (3H, s), 4.23–4.40 (1H, m), 5.12 (2H, s), 7.35 (5H, s).

Reference Example 52

Synthesis of α-methyl N-t-butoxycarbonyl-L-glutamate

After adding 10% palladium-carbon (1.1 g) to a methanol solution (30 ml) of the compound (5.2 g) of Reference example 51, the mixture was stirred under hydrogen atmosphere at room temperature for 15 hours. Palladium-carbon was removed by filtration using Celite and the solvent was removed under reduced pressure. The residue obtained was dissolved in a saturated aqueous sodium hydrogen carbonate solution and the solution was washed with chloroform. After separating the aqueous layer, it was adjusted to pH=4 with 5% citric acid and extracted with chloroform. The chloroform layer was dried over sodium sulfate, and the solvent was removed under reduced pressure to obtain the title compound (3.9 g).

$^1$H-NMR (CDCl$_3$, δ): 1.44 (9H, s), 1.89–2.04 (1H, m), 2.09–2.27 (1H, m), 2.33–2.59 (2H, m), 3.75 (3H, S), 4.24–4.44 (1H, m), 5.17–5.21 (1H, m), 9.38 (1H, bs).

Reference Example 53

Synthesis of methyl 4-amino-n-butyrate hydrochloride

Into a methanol solution (20 ml) of 4-amino-n-butyric acid (1.0 g) was passed through a hydrogen chloride gas for 10 minutes and the mixture was stirred at room temperature for 5 hours. The solvent was removed under reduced pressure to obtain the title compound (1.5 g).

$^1$H-NMR (DMSO-d$_6$, δ): 1.83–2.24 (2H, m), 2.32–2.60 (2H, m), 2.76–3.26 (2H, m), 3.61 (3H, s), 8.26 (2H, bs).

Reference Example 54

Synthesis of α-methyl N-t-butoxycarbonyl-N'-(3-methoxycarbonylpropyl)-L-glutaminate To a tetrahydrofuran solution (5 ml) of the compound (518 mg) of Reference example 52 and triethylamine (0.33 ml) was added a tetrahydrofuran solution (1 ml) of isobutyl chlorocarbonate (0.31 ml) at −20° C. under nitrogen atmosphere, and the mixture was stirred for 30 minutes. Then, after adding a tetrahydrofuran suspension (5 ml) of the compound (366 mg) of Reference example 53 and triethylamine (0.33 ml) to the mixture, the mixture was stirred for one hour. The mixture was gradually returned to room temperature and further stirred for 24 hours. The solvent was removed under reduced pressure and the residue obtained was dissolved in ethyl acetate. The ethyl acetate layer was washed successively with a 5% citric acid aqueous solution, a saturated aqueous sodium hydrogen carbonate solution and water, and dried over sodium sulfate. The solvent was removed under reduced pressure and the residue obtained was subjected to silica gel column chromatography by using chloroform:methanol=99:1 as an eluent to obtain the title compound (575 mg).

$^1$H-NMR (CDCl$_3$, δ): 1.44 (9H, s), 1.78–1.99 (3H, m), 2.16–2.19 (1H, m), 2.22–2.31 (2H, m), 2.39 (2H, t, J=7.1 Hz), 2.70 (2H, q, J=6.5 Hz), 3.68 (3H, s), 3.74 (3H, s), 4.14–4.31 (1H, m), 5.35 (1H, bs), 6.43 (1H, bs).

Reference Example 55

Synthesis of α-methyl N'-(3-methoxycarbonylpropyl)-L-glutaminate trifluoroacetate The compound (726 mg) of Reference example 54 was dissolved in trifluoroacetic acid (2 ml) under ice-cooling and the mixture was stirred for one hour. The solvent was removed under reduced pressure to obtain the title compound (754 mg).

$^1$H-NMR (CDCl$_3$:CD$_3$OD=20:1, δ): 0.92 (2H, quint, J=6.3 Hz), 2.04–2.42 (4H, m), 2.50 (2H, t, J=6.3 Hz), 3.17–3.24 (2H, m), 3.67 (3H, s), 3.81 (3H, s), 4.09–4.15 (1H, m), 7.44 (1H, t, J=6.0 Hz).

Reference Example 56

Synthesis of α-methyl N-(1-carbobenzoxyindolin-5-carbonyl)-N'-(3-methoxycarbonylpropyl)-L-glutaminate By adding thionyl chloride (5 ml) to 1-carbobenzoxyindolin-5-carboxylic acid (599 mg) and the mixture was stirred at room temperature for 2 hours. Then, the mixture was evaporated to dryness under reduced pressure. The solid material obtained was dissolved in methylene chloride (7 ml), and to the solution was added an aqueous solution (3 ml) of the compound (754 mg) of Reference example 55 and sodium hydrogen carbonate (534 mg) at room temperature and the mixture was stirred for 15 hours. Sodium hydrogen carbonate was added to the mixture until pH became 8 and insolubles were removed by filtration using Celite, and the methylene chloride layer was collected by separation. The methylene chloride layer was washed successively with 1N-hydrochloric acid and water, and dried over sodium sulfate. The solvent was removed under reduced pressure and the residue obtained was subjected to silica gel column chromatography using chloroform:methanol=99:1 as an eluent to obtain the title compound (474 mg).

$^1$H-NMR (CDCl$_3$, δ): 1.81 (2H, quint, J=7.0 Hz), 2.09–2.27 (4H, m), 2.34 (2H, t, J=7.3 Hz), 3.15 (2H, t, J=9.0 Hz), 3.27 (2H, t, J=5.4 Hz), 3.65 (3H, s), 3.77 (3H, s), 4.10 (2H, t, J=8.8 Hz), 4.65–4.75 (1H, m), 5.28 (2H, s), 6.38–6.45 (1H, m), 7.36–7.46 (6H, m), 7.66–7.68 (2H, m).

Reference Example 57

Synthesis of α-methyl N-(indolin-5-carbonyl)-N'-(3-methoxycarbonylpropyl)-L-glutaminate After adding 10% palladium-carbon (90 mg) to a methanol solution (10 ml) of the compound (470 mg) of Reference example 56, the mixture was stirred under hydrogen atmosphere at room temperature for 15 hours. After removing palladium-carbon by filtration using Celite, the solvent was removed under reduced pressure to obtain the title compound (350 mg).

$^1$H-NMR (CDCl$_3$, δ): 1.66–2.48 (8H, m), 2.81–3.30 (4H, m), 3.50 (2H, t, J=6.0 Hz), 3.64 (3H, s), 3.73 (3H, s), 4.49–4.81 (1H, m), 6.51 (2H, d, J=9.0 Hz), 6.62–6.84 (1H, m), 7.21–7.33 (1H, m), 7.42–7.57 (2H, m).

Example 28

Synthesis of α-methyl N-[1-[(2,4-diamino-6-pteridinyl)methyl]-indolin-5-carbonyl]-N'-(3-methoxycarbonylpropyl)-L-glutaminate In dimethylacetamide (7 ml) were suspended the compound (350 mg) of Reference example 7 and 6-bromomethyl-2,4-diaminopteridine hydrobromide.isopropanol adduct (414 mg), and the suspension was stirred at room temperature for 24 hours. To the mixture was added triethylamine (0.29 ml) and the mixture was stirred for 10 minutes, it was subjected to silica gel column chromatography by using, as eluents, ethyl acetate and then chloroform:methanol=9:1 as an eluent to obtain the title compound (263 mg).

$^1$H-NMR (DMSO-d$_6$:CDCl$_3$=7:3, δ): 1.67 (2H, quint, J=6.9 Hz), 1.91–2.14 (2H, m), 2.19–2.33 (4H, m), 2.97–3.13 (4H, m), 3.56–3.59 (5H, m), 3.65 (3H, s), 4.34–4.44 (1H, m), 4.55 (2H, s), 6.67 (1H, d, J=8.3 Hz), 7.32 (4H, bs), 7.62–7.66 (2H, m), 7.84 (1H, t, J=8.3 Hz), 8.33 (1H, d, J=7.3 Hz), 8.71 (1H, s).

Example 29

Synthesis of N-[1-[(2,4-diamino-6-pteridinyl)methyl]-indolin-5-carbonyl]-N'-(3-carboxypropyl)-L-glutamine To a methanol (5 ml) solution of the compound (250 mg) of Example 28 was added 1N-sodium hydroxide aqueous solution (0.95 ml) and the mixture was stirred at room temperature for 20 hours. While maintaining the temperature of water bath to 30° C. or lower, the solvent was removed under reduced pressure. The residue obtained was subjected to silica gel column chromatography using chloroform:methanol:28% aqueous ammonia=5:4:1 as an eluent to obtain brownish solid material. The solid material obtained was dissolved in water and insolubles were filtered off, and the solution was adjusted to pH=3.7 with 1N-hydrochloric acid. Deposited brownish precipitates were collected by filtration to obtain the title compound (144 mg).

$^1$H-NMR (DMSO-d$_6$:CDCl$_3$=9:1, δ): 1.61 (2H, quint, J=7.0 Hz), 1.89–2.08 (2H, m), 2.13–2.30 (4H, m), 2.95–3.10 (4H, m), 3.58 (2H, t, J=8.0 Hz), 4.25–4.38 (1H, m), 4.55 (2H, s), 6.70 (1H, d, J=8.3 Hz), 7.61–7.65 (2H, m), 7.85 (1H, t, J=5.8 Hz), 8.21 (1H, d, J=7.3 Hz), 8.73 (1H, s).

Example 30

Synthesis of ammonium N-[1-[(2,4-diamino-6-pteridinyl)methyl]-indolin-5-carbonyl]-homocysteate To a benzene suspension (6 ml) of homocysteic acid hydrobromide (330 ml) were added triethylamine (870 μl) and chlorotrimethyl silane (630 μl) under nitrogen atmosphere, and the mixture was stirred at room temperature for 3 days. Deposited precipitates were filtered off and the filtrate was condensed to obtain silylated homocysteic acid (450 mg). Under a nitrogen atmosphere, in dimethylformamide (18 ml) were dissolved dimethyl cyanophosphonate (213 μl) and triethylamine (172 μl), and 1-[(2,4-diamino)-6-pteridinyl)methyl]indolin-5-carboxylic acid (170 mg) was added little by little at room temperature and the mixture was stirred at the same temperature for 3 hours. To the solution was added a dimethylformamide solution (2 ml) of silylated homocysteic acid (450 mg) and the mixture was stirred at room temperature for 2 days. Then, water (1 ml) was added to the reaction mixture and the solvent was removed under reduced pressure. To the residue was added 3% ammonium bicarbonate aqueous solution and after removing insolubles by filtration, the filtrate was applied to DEAE-cellulose column, washed with water and eluted by 3% ammonium bicarbonate aqueous solution to obtain the title compound (18 mg).

$^1$H-NMR (D$_2$O, δ): 2.0–2.4 (2H, m), 3.15 (4H, m), 3.49 (2H, m), 4.34 (1H, m), 4.49 (2H, s), 6.66 (1H, m), 7.55 (2H, m), 8.69 (1H, s).

Reference Example 58

Synthesis of methyl 3,4-dihydro-2H-1,4-benzothiazinecarboxylate

A mixture of 2-aminobenzothiazol-6-carboxylic acid (15 g), potassium hydroxide (22 g) and water (22 g) was refluxed under a nitrogen atmosphere for 3 hours. The mixture was cooled to room temperature, and water (20 ml), 1,2-dibromoethane (40 ml) and hexadecyltributylphosphonium bromide (3 g) were added thereto and the mixture was refluxed for 6 hours. The mixture was cooled to room temperature, water and chloroform were added thereto and insolubles were removed by decantation. The aqueous layer was adjusted to pH=3 with hydrochloric acid and the chloroform layer was collected by separation. The chloroform layer obtained was washed with a saturated saline solution and dried over anhydrous sodium sulfate. The solvent was removed under reduced pressure and the residue was dissolved in methanol. To the solution was passed through a hydrogen chloride gas for 10 minutes and the mixture was stirred at room temperature overnight. To the residue obtained by removing the solvent under reduced pressure were added water and ethyl acetate, and the aqueous layer was adjusted to pH=5 with 1N sodium hydroxide aqueous solution and then extracted with ethyl acetate. The organic layer obtained was washed with a saturated saline solution and dried over anhydrous sodium sulfate. The solvent was removed under reduced pressure and the residue was subjected to silica gel column chromatography by using ethyl acetate:hexane=1:4 as an eluent to obtain the title compound (721 mg).

$^1$H-NMR (CDCl$_3$, δ): 2.9–3.1 (2H, m), 3.6–3.9 (2H, m), 3.83 (3H, s), 4.0–5.0 (1H, br), 6.39 (1H, d, J=8.4 Hz), 7.45–7.75 (2H, m).

Reference Example 59

Synthesis of N-carbobenzoxy-3,4-dihydro-2H-1,4-benzothiazine-7-carboxylic acid

The compound (313 mg) of Reference example 58 was dissolved in tetrahydrofuran (10 ml) and to the solution was gradually added sodium hydride (180 mg), and the mixture was stirred at room temperature for 20 minutes. Then, carbobenzoxy chloride (1.3 ml) was added to the mixture and the mixture was stirred overnight. After adding water to the mixture, the mixture was extracted with ethyl acetate. The organic layer obtained was dried over anhydrous sodium sulfate and then the solvent was removed under reduced pressure. The residue was applied to silica gel column chromatography by using ethyl acetate:hexane=1:10 as an eluent, and methyl N-carbobenzoxy-3,4-dihydro-2H-1,4-benzothiazine-7-carboxylate obtained was suspended in ethanol (15 ml). To the suspension was added 1N-sodium hydroxide aqueous solution (1.9 ml) and the mixture was stirred overnight. The solvent was removed under reduced pressure, and the residue obtained was dissolved in water (20 ml). Then, 1N-hydrochloric acid was gradually added to adjust pH=3 and the mixture was extracted with chloroform. The organic layer was washed with a saturated saline solution and dried over anhydrous sodium sulfate. The residue obtained by removing the solvent under reduced pressure was applied to silica gel column chromatography by using chloroform:methanol=95:5 as an eluent to obtain the title compound (208 mg).

$^1$H-NMR (CDCl$_3$:CD$_3$OD=9:1, δ): 3.0–3.3 (2H, m), 3.8–4.1 (2H, m), 5.25 (2H, s), 7.3–7.9 (8H, m).

Reference Example 60

Synthesis of diethyl N-(3,4-dihydro-2H-1,4-benzothiazine-7-carbonyl)-L-glutamate To a dimethylformamide solution (5 ml) containing the compound (208 mg) of Reference example 59, diethyl L-glutamate hydrochloride (151 mg), 1-hydroxybenzotriazole (90 mg) and N-methylmorpholine (70 μl) was added dicyclohexylcarbodiimide (145 mg) under ice-cooling, and the mixture was stirred at the same temperature for one hour and then at room temperature for overnight. To the mixture was added ethyl acetate, and precipitates were filtered off and the filtrate was washed successively with an aqueous sodium hydrogen carbonate solution and a saturated saline solution and dried over anhydrous sodium sulfate. The residue obtained by removing the solvent under reduced pressure was applied to silica gel column chromatography by using ethyl acetate:hexane=1:2 as an eluent, and diethyl N-[N'-carbobenzoxy-3,4-dihydro-2H-1,4-benzothiazine-7-carbonyl]-L-glutamate obtained was dissolved in ethanol (20 ml). After adding 10% palladium-carbon (700 mg) to the solution, the solution was stirred under hydrogen atmosphere at room temperature overnight. Palladium-carbon was removed by filtration using Celite, and the solvent was removed under reduced pressure. The residue obtained was subjected to silica gel column chromatography by using a mixed solvent of ethyl acetate:hexane=2:3 as an eluent to obtain the title compound (83 mg).

$^1$H-NMR (CDCl$_3$:CD$_3$OD=9:1, δ): 1.25 (6H, m), 2.0-2.7 (4H, m), 2.9-3.1 (2H, m), 3.6-3.8 (2H, m), 3.9-4.4 (5H, m), 6.45 (1H, d, J=8.0 Hz), 7.2-7.6 (2H, m).

Example 31

Synthesis of diethyl N-[1-[((2,4-diamino)-6-pteridinyl)methyl]-3,4-dihydro-2H-1,4-benzothiazine-7-carbonyl]-L-glutamate In dimethylacetamide (3 ml) were suspended the compound (83 mg) of Reference example 60 and 6-bromomethyl-2,4-diaminopteridine hydrobromide.isopropanol adduct (85 mg), and the suspension was stirred at 60° C. for 3 hours and then at 100° C. for 30 minutes. After cooling, the reaction mixture was poured into a saturated aqueous sodium hydrogen carbonate solution and extracted three times with chloroform. The organic layer was dried over anhydrous sodium sulfate and the solvent was removed under reduced pressure. The residue obtained was applied to silica gel column chromatography by using a mixed solvent of chloroform:methanol=93:7 as an eluent to obtain the title compound (21 mg).

$^1$H-NMR (CDCl$_3$:CD$_3$OD=9:1, δ): 1.26 (6H, m), 2.0-2.3 (2H, m), 2.46 (2H, m), 3.12 (2H, m), 3.91 (2H, m), 4.1-4.3 (4H, m), 4.62 (1H, m), 4.78 (2H, s), 6.69 (1H, d, J=8.9 Hz), 7.04 (1H,m), 7.60 (1H, d, J=2.2 Hz), 8.66 (1H, s).

Example 32

Synthesis of N-[1-[((2,4diamino)-6-pteridinyl)methyl]-3,4-dihydro-2H-1,4-benzothiazine-7-carbonyl]-L-glutamic acid The compound (20 mg) of Example 31 was dissolved in ethanol (2 ml), and 1N-sodium hydroxide aqueous solution (170 μl) was added to the solution at 35° C. and the mixture was stirred at the same temperature for 4 hours. After continuing stirring at 25° C. for 20 hours, water (0.5 ml) was added to the reaction mixture and ethanol was removed under reduced pressure. The residue obtained was dissolved in water (6 ml), adjusted to pH=3.7 with 1N-hydrochloric acid under ice-water cooling and allowed to stand overnight at cool place. Deposited precipitates were collected by filtration to obtain the title compound (18 mg).

$^1$H-NMR (DMSO-d$_6$, δ): 1.8-2.2 (2H, m), 2.30 (2H, m), 3.18 (2H, m), 3.95 (2H, m), 4.37 (1H, m), 4.76 (2H, s), 6.79 (1H, d, J=8.8 Hz), 7.42 (1H, m), 7.59 (1H, d, J=2.0 Hz), 8.22 (1H, d, J=7.3 Hz), 8.67 (1H, s).

Example 33

Synthesis of N-[1-[(2,4-diamino-6-pteridinyl)methyl]-1-oxo-3,4-dihydro-2H-1,4-benzothiazine-7-carbonyl]-L-glutamic acid The compound (10 mg) of Example 32 was suspended in water (1 ml) and 1N-sodium hydroxide aqueous solution was added thereto to dissolve the mixture. Under ice-cooling, 0.5M sodium metaperiodate (50 μl) was added to the solution and the mixture was stirred at the same temperature for 5 hours. The reaction mixture was adjusted to pH=3.5 and deposited precipitates were collected by filtration to obtain the title compound (4 mg).

$^1$H-NMR (DMSO-d$_6$, δ): 1.8-2.2 (2H, m), 2.33 (2H, m), 2.9-3.3 (2H, m), 3.8-4.0 (1H, m), 4.2-4.5 (2H, m), 4.83 (1H, d, J=17.1 Hz), 5.19 (1H, d, J=17.1 Hz), 7.07 (1H, d, J=9.3 Hz), 7.7-7.9 (1H, m), 8.1-8.2 (1H, m), 8.42 (1H, m), 8.72 (1H, s). IR (KBr) ν max 2800-3600, 1644, 1608, 1552, 1504 and 1008 cm$^{-1}$ FAB MS 515 (M+1)$^+$.

Reference Example 61

Synthesis of benzyl N-t-butoxycarbonyl-N'-methanesulfonylglutaminate

In tetrahydrofuran (268 ml) were dissolved N,N'-carbonyldiimidazole (13.6 g) and α-benzyl [N-(t-butoxycarbonyl)glutamate] (25 g) and the mixture was stirred under ice-cooling for one hour. Then, the solution was added dropwise to a tetrahydrofuran (132 ml) solution containing methanesulfoneamide (20.5 g) and 1,8-diazabicyclo[5.4.0]-7-undecene (32.9 g) under ice-cooling. After dropwise addition, the mixture was returned to room temperature and stirred for 4 days. After adding 500 ml of 1N hydrochloric acid to the mixture, it was extracted with chloroform. The organic layer was dried over anhydrous magnesium sulfate and the solvent was removed under reduced pressure to obtain the title compound (30 mg).

$^1$H-NMR (CDCl$_3$, δ): 1.42 (9H, s), 1.8-2.8 (4H, m), 3.25 (3H, s), 4.32 (1H, m), 5.14 (2H, s), 7.40 (5H, s).

Reference Example 62

Synthesis of benzyl N'-methanesulfonylglutaminate.trifluoroacetate

The compound (4.65 g) of Reference example 61 was dissolved in trifluoroacetic acid (60 ml) and the solution was stirred at room temperature for one hour. Then, the reaction mixture was condensed at 30° C. and triturated by adding ether to obtain the title compound (4.5 g).

$^1$H-NMR (CDCl$_3$, δ): 1.8-2.8 (4H, m), 3.20 (3H, s), 4.50 (1H, m), 5.28 (2H, s), 7.42 (5H, s).

Example 34

Synthesis of benzyl N-[1-[(2,4-diamino-6-pteridinyl)methyl]indolin-5-carbonyl]-N'-methanesulfonylglutaminate In dimethylformamide (18 ml) were dissolved diethyl cyanophosphonate (213 μl) and triethylamine (172 μl) under nitrogen atmosphere, and to the solution was added 1-[(2,4-diamino-6-pteridinyl)methyl]indolin-5-carboxylic acid (160 mg) little by little and the mixture was stirred at the same temperature for 3 hours. To the mixture was added a dimethylformamide solution (3 ml) containing the compound (450 mg) of Reference example 62 and triethylamine (180 μl) and the mixture was stirred at room temperature for 3 days. Then, water (1 ml) was added to the reaction mixture and the solvent was removed under reduced pressure. The residue was subjected to silica gel column chromatography by using a mixed solvent of chloroform:methanol:aqueous ammonia=15:5:1 as an eluent to obtain the title compound (60 mg).

$^1$H-NMR (DMSO-d$_6$, δ): 1.9–2.1 (2H, m), 2.3–2.5 (2H, m), 2.98 (2H, t, J=8.6 Hz), 3.28 (3H, s), 3.55 (2H, t, J=8.6 HZ), 4.21 (1H, m), 4.53 (2H, s), 5.04 (2H, s), 6.71 (1H, J=8.6 Hz), 7.34 (5H, s), 7.55 (2H, m), 8.72 (1H, s).

Example 35

Synthesis of
N-[1-[(2,4-diamino-6-pteridinyl)methyl]indolin-5-carbonyl]-N'-methanesulfonylglutamine The compound (25 mg) of Example 34 was suspended in ethanol (5 ml), and 1N-sodium hydroxide aqueous solution (200 μl) was added to the suspension and the mixture was stirred at room temperature overnight. Then, water (0.5 ml) was added to the mixture and ethanol was removed under reduced pressure. The residue obtained was dissolved in water (6 ml) and the solution was adjusted to pH=3.7 with 1N-hydrochloric acid under ice-water cooling and allowed to stand at cold place overnight. Deposited precipitates were collected by filtration to obtain the title compound (20 mg).

$^1$H-NMR (DMSO-d$_6$, δ): 1.9–2.1 (2H, m), 2.2–2.4 (2H, m), 3.00 (2H, t, J=8.6 Hz), 3.19 (3H, s), 3.60 (2H, t, J=8.6 Hz), 4.35 (1H, m), 4.56 (2H, s), 6.70 (1H, d, J=8.6 Hz), 7.63 (2H, m), 8.75 (1H, s).

What is claimed is:

1. A compound represented by the formula:

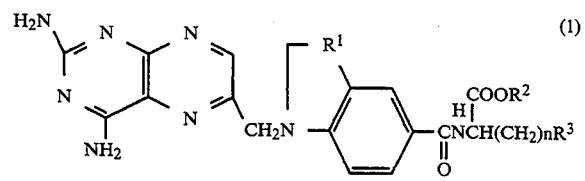

wherein R$^1$ represents one selected from the group consisting of CH$_2$, CH$_2$CH$_2$, CH$_2$O, CH$_2$S and CH$_2$SO; R$^2$ represents hydrogen atom, a lower alkyl group having 1 to 4 carbon atoms or a benzyl group; n represents an integer of 1 to 4; R$^3$ represents a group represented by the formula: COOR$^4$ (where R$^4$ represents hydrogen atom or a lower alkyl group having 1 to 4 carbon atoms), NHCOR$^5$ (where R$^5$ represents a phenyl group which may be substituted), CONR$^6$R$^7$ (where R$^6$ represents hydrogen atom or a lower alkyl group having 1 to 4 carbon atoms; R$^7$ represents a lower alkyl group having 1 to 4 carbon atoms, a phenyl group or a carboxylalkyl group each of which may be substituted or a lower alkylsulfonyl group), PO$_3$H$_2$ or SO$_3$H.

2. The compound according to claim 1, wherein R$^3$ is COOR$^4$ (R$^4$ has the same meaning as defined in claim 1), PO$_3$H$_2$ or SO$_3$H.

3. The compound according to claim 1, wherein R$^3$ is NHCOR$^5$ (R$^5$ has the same meaning as defined in claim 1).

4. The compound according to claim 1, wherein R$^3$ is CONR$^6$R$^7$ (R$^6$ and R$^7$ have the same meanings as defined in claim 1).

5. An antirheumatic pharmaceutical composition comprising a pharmaceutically acceptable excipient and an antirheumatic-effective ingredient, of the compound according to claim 1.

6. In a psoriasis curing pharmaceutical composition comprising a pharmaceutically acceptable excipient and a psoriasis curing-effective ingredient of the compound according to claim 1.

7. In a carcinostatic pharmaceutical composition comprising a pharmaceutically acceptable excipient and a carcinostatic-effective ingredient of the compound according to claim 1.

* * * * *